US006987127B2

(12) United States Patent
Kennedy

(10) Patent No.: US 6,987,127 B2
(45) Date of Patent: Jan. 17, 2006

(54) REGULATION OF NAD(P)H OXIDASE GROWTH AND TRANSCRIPTION IN MELANOMA CELLS

(75) Inventor: Thomas Preston Kennedy, Charlotte, NC (US)

(73) Assignee: Charlotte-Mecklenburg Hospital Authority, Charlotte, NC (US)

( * ) Notice: Subject to any disclaimer, the term of this patent is extended or adjusted under 35 U.S.C. 154(b) by 0 days.

(21) Appl. No.: 10/493,936

(22) PCT Filed: Dec. 19, 2002

(86) PCT No.: PCT/US02/41016

§ 371 (c)(1),
(2), (4) Date: Aug. 3, 2004

(87) PCT Pub. No.: WO03/055473

PCT Pub. Date: Oct. 7, 2003

(65) Prior Publication Data

US 2005/0215624 A1      Sep. 29, 2005

Related U.S. Application Data

(60) Provisional application No. 60/342,839, filed on Dec. 21, 2001.

(51) Int. Cl.
A61K 31/35       (2006.01)
A61K 31/12       (2006.01)

(52) U.S. Cl. ..................... 514/457; 514/681
(58) Field of Classification Search ............... 514/457, 514/681
See application file for complete search history.

(56) References Cited

U.S. PATENT DOCUMENTS 5,120,537 A  *  6/1992  Esmon et al. ............ 424/94.64
5,576,338 A  *  11/1996  Friesen et al. ............... 514/337
5,668,114 A       9/1997  Birkmayer
5,753,702 A  *  5/1998  Bednar et al. ............... 514/552
5,763,496 A       6/1998  Holland
5,939,460 A       8/1999  Ternansky et al.
6,593,493 B1 *  7/2003  Ardecky et al. ............. 562/465
6,660,767 B2 * 12/2003  Jacobs et al. ................ 514/457

OTHER PUBLICATIONS

Cecil Textbook of Medicine, 21st Ed., vol. 1, Goldman et al. (eds.), published 2000 by W.B. Saunders Co., pp 1060-1074.*

* cited by examiner

Primary Examiner—Raymond J. Henley, III
(74) Attorney, Agent, or Firm—Alston & Bird LLP

(57) ABSTRACT

Malignant melanoma cells spontaneously generate reactive oxygen species (ROS) that promote constitutive activation of the transcription factor nuclear factor-kB (NF-kB). Although antioxidants and inhibitors of NAD(P)H oxidases significantly reduce constitutive NF-kB activation and suppress cell proliferation, the nature of the enzyme responsible for ROS production in melanoma cells has not been determined. To address this issue, we now have characterized the source of ROS production in melanoma cells. ROS are generated by isolated, cytosol-free melanoma plasma membranes, with inhibition by NAD(P)H oxidase inhibitors. The $p22^{phox}$, $gp91^{phox}$ and $p67^{phox}$ components of the human phagocyte NAD(P)H oxidase, and the $91^{phox}$ homolog NOX4 were demon-strated in melanomas by RT-PCR and sequencing, and protein product for both $p22^{phox}$ and $gp91^{phox}$ were detected in cell membranes by immunoassay. Normal human epidermal melanocytes expressed only $p22^{phox}$ and NOX4. Melanoma proliferation was reduced by NAD(P)H oxidase inhibitors and by transfection of antisense but not sense oligonucleotides for $p22^{phox}$ and NOX4. Also, the flavoprotein inhibitor diphenylene iodonium inhibited constitutive DNA binding of nuclear protein to the NF-kB and cyclic-AMP response element consensus oligonucleotides, without affecting DNA binding activity to AP-1 or OCT-1.

9 Claims, 10 Drawing Sheets

A

SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
accaccatgg agaaggctgg        20

<210> SEQ ID NO 2
<211> LENGTH: 20
<212> TYPE: DNA

```
<213> ORGANISM: Artificial Sequence
<220> FEATURE:
<223> OTHER INFORMATION: PCR primer

<400> SEQUENCE: 2
ctcagtgtag cccaggatgc                                                      20

<210> SEQ ID NO 3
<211> LENGTH: 27
<212> TYPE: DNA
<213> ORGANISM: Artificial Sequence
<220> FEATURE:
<223> OTHER INFORMATION: PCR primer

<400> SEQUENCE: 3
atggagcgct ggggacagaa gcacatg                                              27

<210> SEQ ID NO 4
<211> LENGTH: 24
<212> TYPE: DNA
<213> ORGANISM: Artificial Sequence
<220> FEATURE:
<223> OTHER INFORMATION: PCR primer

<400> SEQUENCE: 4
gatggtgcct ccgatctgcg gccg                                                 24

<210> SEQ ID NO 5
<211> LENGTH: 24
<212> TYPE: DNA
<213> ORGANISM: Artificial Sequence
<220> FEATURE:
<223> OTHER INFORMATION: PCR primer

<400> SEQUENCE: 5
tcaataattc tgatccttat tcag                                                 24

<210> SEQ ID NO 6
<211> LENGTH: 24
<212> TYPE: DNA
<213> ORGANISM: Artificial Sequence
<220> FEATURE:
<223> OTHER INFORMATION: PCR primer

<400> SEQUENCE: 6
tgttcacaaa ctgttatatt atgc                                                 24

<210> SEQ ID NO 7
<211> LENGTH: 22
<212> TYPE: DNA
<213> ORGANISM: Artificial Sequence
<220> FEATURE:
<223> OTHER INFORMATION: PCR primer

<400> SEQUENCE: 7
ctgggtggtt aaccactggt tt                                                   22

<210> SEQ ID NO 8
<211> LENGTH: 22
<212> TYPE: DNA
<213> ORGANISM: Artificial Sequence
<220> FEATURE:
<223> OTHER INFORMATION: PCR primer

<400> SEQUENCE: 8
gaatccctaa gtgccgtaac ca                                                   22
```

<210> SEQ ID NO 9
<211> LENGTH: 23
<212> TYPE: DNA
<213> ORGANISM: Artificial Sequence
<220> FEATURE:
<223> OTHER INFORMATION: PCR primer

<400> SEQUENCE: 9
taaccaaggg ccagagtatc act                                    23

<210> SEQ ID NO 10
<211> LENGTH: 20
<212> TYPE: DNA
<213> ORGANISM: Artificial Sequence
<220> FEATURE:
<223> OTHER INFORMATION: PCR primer

<400> SEQUENCE: 10
ggccctccca cccatagatt                                        20

<210> SEQ ID NO 11
<211> LENGTH: 20
<212> TYPE: DNA
<213> ORGANISM: Artificial Sequence
<220> FEATURE:
<223> OTHER INFORMATION: PCR primer

<400> SEQUENCE: 11
acccagccag cactatgggt                                        20

<210> SEQ ID NO 12
<211> LENGTH: 20
<212> TYPE: DNA
<213> ORGANISM: Artificial Sequence
<220> FEATURE:
<223> OTHER INFORMATION: PCR primer

<400> SEQUENCE: 12
agtagcctgt gacgtcgtct                                        20

<210> SEQ ID NO 13
<211> LENGTH: 20
<212> TYPE: DNA
<213> ORGANISM: Artificial Sequence
<220> FEATURE:
<223> OTHER INFORMATION: PCR primer

<400> SEQUENCE: 13
cgagggaacc agctgataga                                        20

<210> SEQ ID NO 14
<211> LENGTH: 20
<212> TYPE: DNA
<213> ORGANISM: Artificial Sequence
<220> FEATURE:
<223> OTHER INFORMATION: PCR primer

<400> SEQUENCE: 14
catgtgaaca ctgagcttca                                        20

<210> SEQ ID NO 15
<211> LENGTH: 22
<212> TYPE: DNA
<213> ORGANISM: Artificial Sequence
<220> FEATURE:

```
<223> OTHER INFORMATION: PCR primer

<400> SEQUENCE: 15
ggtcctcacc atggggcaga tc                                        22

<210> SEQ ID NO 16
<211> LENGTH: 22
<212> TYPE: DNA
<213> ORGANISM: Artificial Sequence
<220> FEATURE:
<223> OTHER INFORMATION: PCR primer

<400> SEQUENCE: 16
gatctgcccc atggtgagga cc                                        22

<210> SEQ ID NO 17
<211> LENGTH: 20
<212> TYPE: DNA
<213> ORGANISM: Artificial Sequence
<220> FEATURE:
<223> OTHER INFORMATION: PCR primer

<400> SEQUENCE: 17
tcgaggaggt cctgtgtcgg                                           20

<210> SEQ ID NO 18
<211> LENGTH: 20
<212> TYPE: DNA
<213> ORGANISM: Artificial Sequence
<220> FEATURE:
<223> OTHER INFORMATION: PCR primer

<400> SEQUENCE: 18
agctcctcca ggacacagcc                                           20

<210> SEQ ID NO 19
<211> LENGTH: 22
<212> TYPE: DNA
<213> ORGANISM: Artificial Sequence
<220> FEATURE:
<223> OTHER INFORMATION: PCR primer

<400> SEQUENCE: 19
agttgagggg actttcccag gc                                        22

<210> SEQ ID NO 20
<211> LENGTH: 22
<212> TYPE: DNA
<213> ORGANISM: Artificial Sequence
<220> FEATURE:
<223> OTHER INFORMATION: PCR primer

<400> SEQUENCE: 20
tcaactcccc tgaagggtc cg                                         22

<210> SEQ ID NO 21
<211> LENGTH: 27
<212> TYPE: DNA
<213> ORGANISM: Artificial Sequence
<220> FEATURE:
<223> OTHER INFORMATION: PCR primer

<400> SEQUENCE: 21
agagattgcc tgacgtcaga gagctag                                   27
```

```
<210> SEQ ID NO 22
<211> LENGTH: 27
<212> TYPE: DNA
<213> ORGANISM: Artificial Sequence
<220> FEATURE:
<223> OTHER INFORMATION: PCR primer

<400> SEQUENCE: 22
tctctaacgg actgcagtct ctcgatc                                            27

<210> SEQ ID NO 23
<211> LENGTH: 21
<212> TYPE: DNA
<213> ORGANISM: Artificial Sequence
<220> FEATURE:
<223> OTHER INFORMATION: PCR primer

<400> SEQUENCE: 23
cgcttgatga gtcagccgga a                                                  21

<210> SEQ ID NO 24
<211> LENGTH: 21
<212> TYPE: DNA
<213> ORGANISM: Artificial Sequence
<220> FEATURE:
<223> OTHER INFORMATION: PCR primer

<400> SEQUENCE: 24
gcgaactact cagtcggcct t                                                  21

<210> SEQ ID NO 25
<211> LENGTH: 22
<212> TYPE: DNA
<213> ORGANISM: Artificial Sequence
<220> FEATURE:
<223> OTHER INFORMATION: PCR primer

<400> SEQUENCE: 25
tgtcgaatgc aaatcactag aa                                                 22

<210> SEQ ID NO 26
<211> LENGTH: 22
<212> TYPE: DNA
<213> ORGANISM: Artificial Sequence
<220> FEATURE:
<223> OTHER INFORMATION: PCR primer

<400> SEQUENCE: 26
acagcttacg tttagtgatc tt                                                 22
```

REGULATION OF NAD(P)H OXIDASE GROWTH AND TRANSCRIPTION IN MELANOMA CELLS

CROSS-REFERENCE TO RELATED APPLICATION

This application claims priority to PCT International Application Number PCT/US02/41016 filed on Dec. 19, 2002 and to provisional application U.S. Ser. No. 60/342,839, filed on Dec. 21, 2001, which are incorporated herein by reference.

BACKGROUND OF THE INVENTION

1. Field of the Invention

The present invention relates to a method for inhibiting NAD(P)H oxidase enzymes in producing reactive oxygen species for growth regulation of normal and malignant tissues.

2. Description of Related Art

Reactive oxygen species (ROS) generated by an NAD(P)H oxidase are important signaling molecules for proliferation of normal cells. The role of a signaling NAD(P)H oxidase has been most extensively explored in vascular smooth muscle cells, where both $p22^{phox}$ and the unique $gp91^{phox}$ homolog NOX1 are important for function of an NAD(P)H oxidase activity that mediates angiotensin II-induced superoxide ($O_2$) formation and redox-sensitive signaling pathways (K. K. Griendling et al. (2000) Circ. Res. 86:494–501; B. Lassegue et al. (2001) Circ. Res. 88:888–894). Similar but structurally distinct NAD(P)H oxidases also perform signaling functions in normal vascular endothelial cells (A. Gorlach et al. (2000) Circ. Res. 87:26–32; S. A. Jones et al. (1996) Am. J. Physiol. 271 (Heart Circ Physiol 49): H1626–H1634) and adventitial cells (P. J. Pagano et al. (1997) Proc. Natl. Acad. Sci. USA (1997) 94:14483–14488), and the $gp91^{phox}$ homolog NOX4 has been described in renal tubular epithelium (M. Geiszt et al. (2000) Proc. Natl. Acad. Sci. USA 97:8010–8014; A. Shiose et al. (2001) J. Biol. Chem. 276:1417–1423), fetal tissue (G. Cheng et al. (2001) Gene 269:131–140), placenta (G. Cheng et al., supra.), and proliferating vascular smooth muscle (13. Lassegue, et al. supra.).

Like normal cells, human tumor cells also produce substantial amounts of ROS spontaneously (B. Del Bello et al. (1999) FASEB J., 13:69–79; D. J. Morre et al. (1995) Proc. Natl. Acad. Sci. USA, 92:1831–1835; T. P. Szatrowski et al. (1991) Cancer Res. 51:794–798), and evidence points to a role for these ROS in signaling neoplastic proliferation. Mitogenic signaling through both Ras (K. Irani et al. (1997) Science 275:1649–1652) and Rac (T. Joneson et al. (1998) J. Biol. Chem. 273:17991–17994) is mediated by $O_2^-$, and transfection with mitogenic oxidase NOX1 transforms normal fibroblasts (Y-A. Suh et al. (1999) Nature 410:79–82) and creates cell lines that are tumorigenic in athymic mice (R. Arnold et al. (2001) Proc. Natl. Acad. Sci. USA 98:5550–5555). The NOX1 homolog has been found expressed in the CaCo human colon carcinoma cells (G. Cheng et al., supra; H. Kikuchi et al., (2000) Gene 254: 237–243; Y-A. Suh et al, supra) and HepG2 hepatoma cells (H. Kikuchi et al., supra), and $gp91^{phox}$ expression has been demonstrated in small cell lung cancer (D. Wang et al., (1996) Proc. Natl. Acad. Sci. USA 93:13182–13187). However, a potential role for a phagocyte-like NAD(P)H membrane oxidase in signaling proliferation of malignant melanoma cells has not been previously demonstrated.

S. S. Brar and co-workers reported that endogenously produced ROS signal constitutive activation of NF-κB and cellular proliferation in M1619 malignant melanoma cells. Based upon inhibition of these events by the NAD(P)H: quinone oxidoreductase (NQO) inhibitor dicumarol, S. S. Brar and co-workers speculated that cytosolic NQO might provide the enzymatic source of electrons for reduction of membrane ubiquinone to ubiquinol, with subsequent generation of superoxide ($O_2^-$) from molecular oxygen. However, dicumarol also inhibited growth of H596 non-small-cell lung cancer cells (S. S. Brar et al. (2001) Am. J. Physiol. Cell Physiol. 280:C659–C676). H596 cells express a mutant NQO protein and have elevated mRNA for NQO but no detectable enzymatic activity (R. D. Traver et al. (1997) Brit. J. Cancer 75:69–75).

SUMMARY OF THE INVENTION

It is an object of the invention to provide a method of inhibiting NAD(P)H oxidase enzymes.

Another object of this invention is to provide a method for a growth-regulatory oxidase activity in human malignant melanoma cells.

It has been found that that the generation of intracellular reactive oxygen species in melanomas is inhibited by diphenylene iodonium, coumarin and coumarin analogs and derivatives such as dicumarol. For example, it has been found that dicumarol inhibits $O_2$ generation by isolated plasma membranes lacking a cytosolic source of NQO. M1619, other malignant melanomas and normal human epidermal melanocytes express mRNA for the $p22^{phox}$ membrane subunit of the NAD(P)H oxidase and melanomas express $gp91^{phox}$. Melanomas and melanocytes also express the $gp91^{phox}$ homolog NOX4, which has been recently found in renal tubular epithelial cells and renal cell carcinomas (R. L. Shattuck-Brandt et al., (1997) Cancer Res. 57:3032–3039), glioblastomas (G. Cheng et al., supra) and CaCo colon cancer cells (G. Cheng et al., supra). Finally, membrane $O_2$ generation and melanoma proliferation are reduced by inhibitor strategies directed at the leukocyte NAD(P)H oxidase. It is thought that a form of this same enzyme system serves as a growth regulatory oxidase in malignant melanoma cells.

Consideration of the specification, including the several figures and examples to follow will enable one skilled in the art to determine additional objects and advantages of the invention.

BRIEF DESCRIPTION OF THE DRAWINGS

FIG. 3 shows proliferating malignant melanoma cells express $p22^{phox}$, $gp91^{phox}$, NOX4 and $p67^{phox}$.

FIG. 4 shows that antisense oliogonucleotides for NAD(P)H oxidase components inhibit melanoma cell proliferation.

FIG. 5 shows NF-κB activation in melanomas is inhibited by the NAD(P)H oxidase inhibitor diphenylene iodonium.

FIG. 6 shows that inhibition of NF-κB does not reduce melanoma proliferation. FIG. 7 shows NAD(P)H Oxidase inhibition reduces DNA binding to the cyclic-AMP responsive element (CRE) but not to AP-1 or OCT-1.

DETAILED DESCRIPTION OF THE INVENTION

The present invention may be understood more readily by reference to the following detailed description of specific embodiments and the Examples and Figures included therein.

As used herein the following abbreviations shall mean: ROS, reactive oxygen species; DPI, diphenylene iodonium; $O_2^-$, superoxide anion; RT-PCT, reverse transcriptase polymerase chain reaction; NF-κB, nuclear factor-κB; IκBα, inhibitor of NF-κB; CRE, cyclic-AMP response element; AP-1, activator protein-1; NQO, NAD(P)H quinone oxidoreductase; HEPES, N-2-hydroxyethylpiperazine-N'-2-ethanesulfonic acid; EDTA, ethylenediaminetetraacetic acid; FBS, fetal bovine serum; EMSA, electrophoretic mobility shift assay; HBSS, Hanks' balanced salt solution; MTT, 3-[4,5-dimethylthiazol]-2yl-2,5-diphenyl tetrazolium bromide; DPBS, Dulbecco's phosphate-buffered saline; DMSO, dimethylsulfoxide; SOD, superoxide dismutase; PMSF, phenylmethylsulfonyl fluoride; GAPDH, glyceraldehydes phosphate dehydrogenase.

Figure 3A:
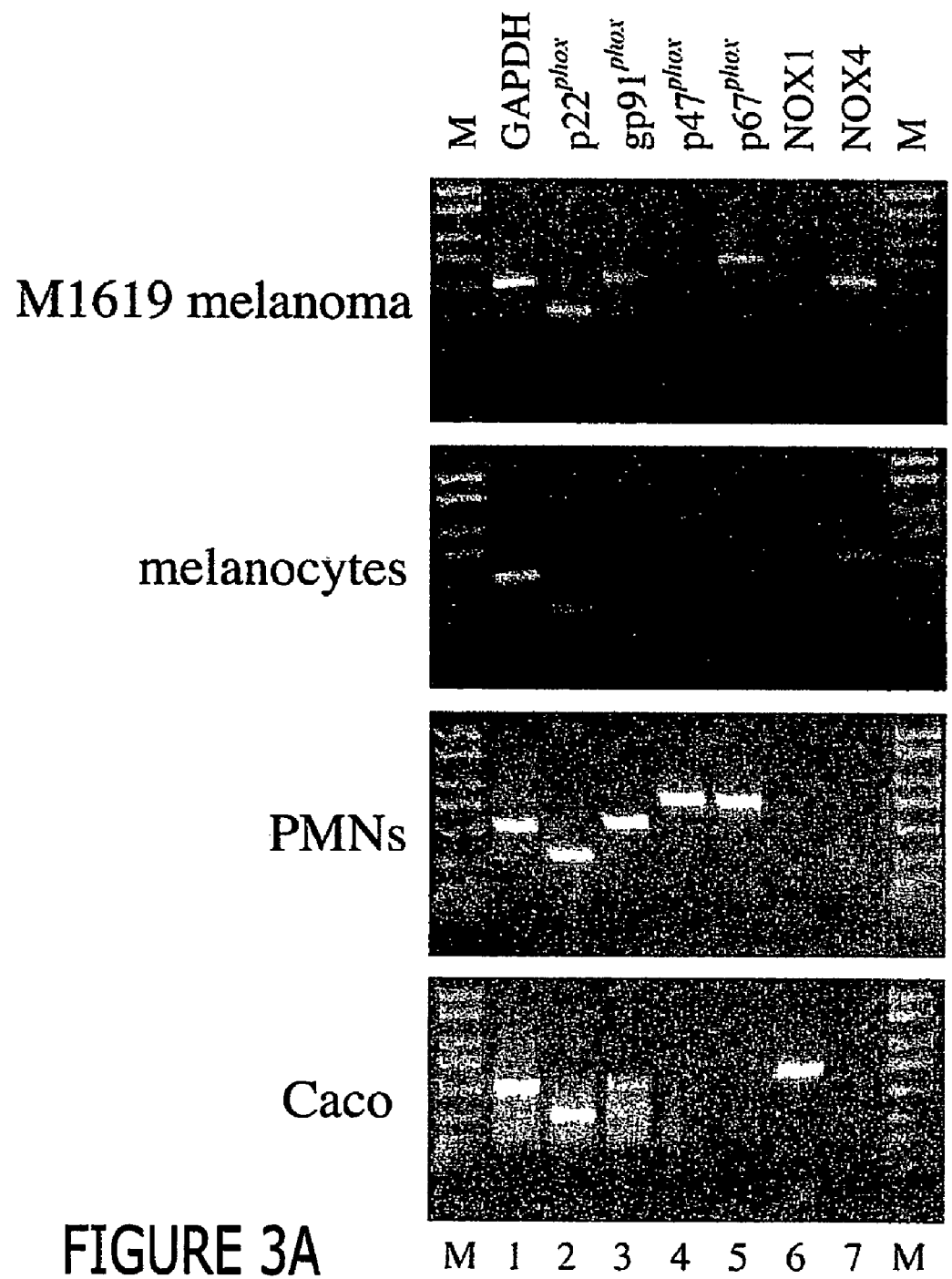
FIG. 3A shows RT-PCR performed on nearly confluent M1619 melanoma cells and normal human epidermal melanocytes.
Figure 3C:
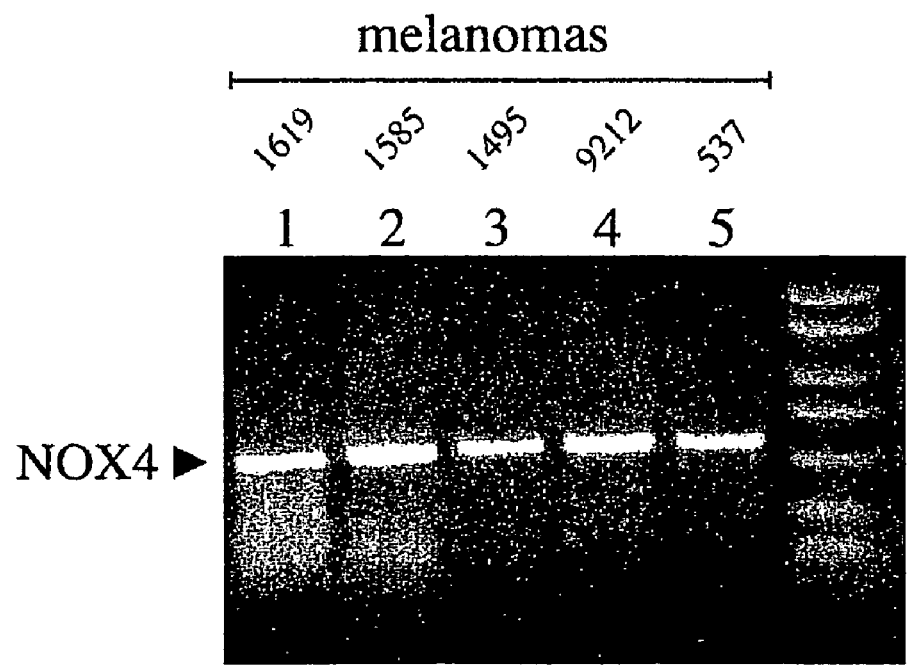
FIG. 3C shows malignant melanoma cells express NOX4.
Figure 4A:
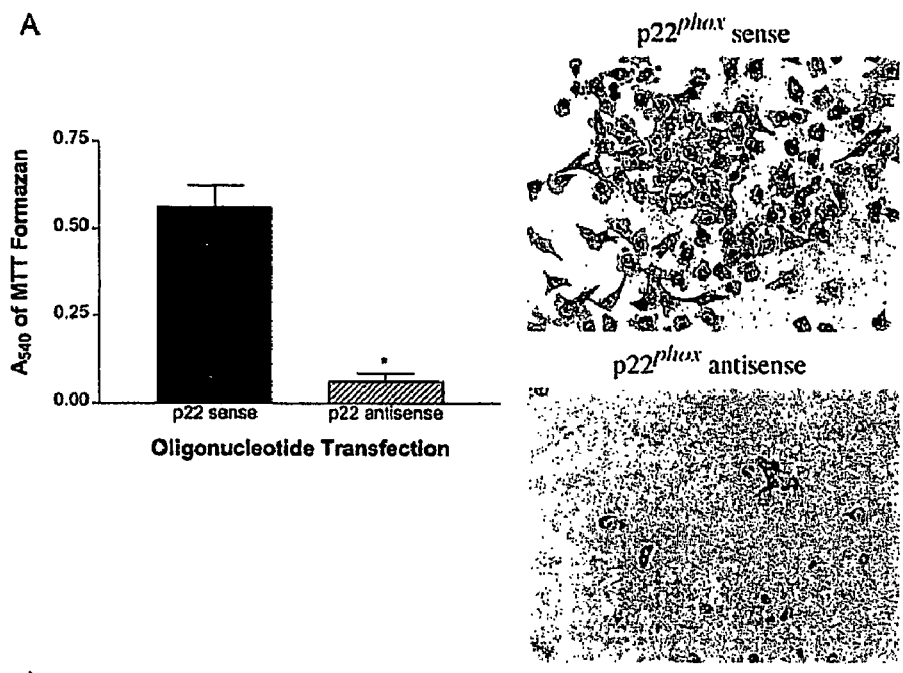
FIG. 4A shows that antisense oligonucleotides for $p22^{phox}$ block melanoma growth.
Figure 4B:
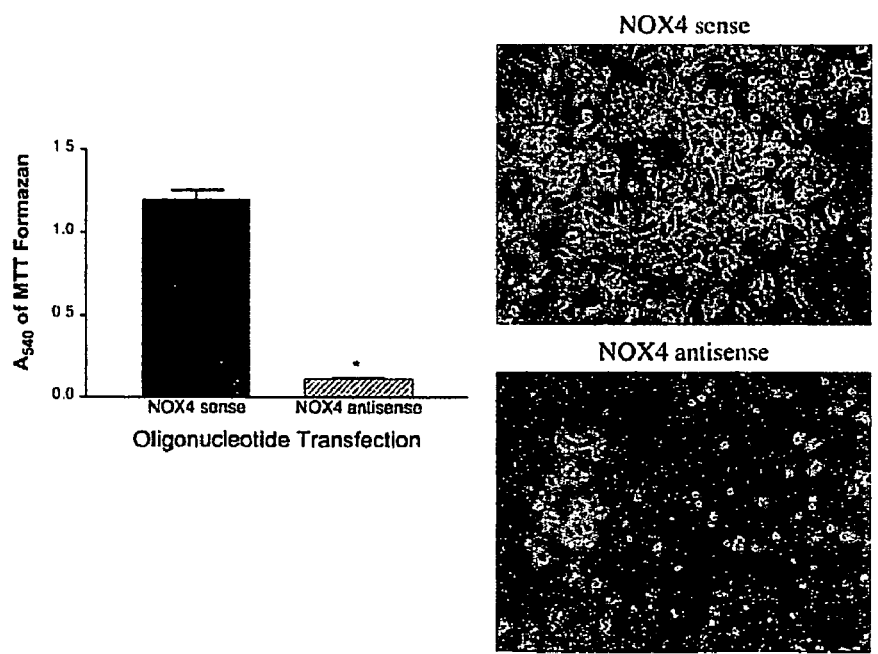
FIG. 4B shows that antisense oligonucleotides for NOX4 block melanoma growth.

This invention demonstrates evidence for a growth-regulatory oxidase activity in human malignant melanoma cells. More specifically, it has been found that that the generation of intracellular reactive oxygen species in melanomas is inhibited by diphenylene iodonium, coumarin and coumarin analogs and derivatives such as dicumarol. Using RT-PCR it was found that in M1619 melanoma cells for mRNA expression of the NAD(P)H oxidase components $p22^{phox}$, $gp91^{phox}$, the $gp91^{phox}$ homolog NOX4, $p67^{phox}$, and possibly $p47^{phox}$ (FIGS. 3A and 3C). Expression of oxidase components is not necessarily a transforming event in melanomas, since $p22^{phox}$ and NOX4 were also expressed in normal melanocytes. However, several oxidase components appear critically important for malignant growth, since melanoma proliferation is reduced by transfection of antisense but not sense oligonucleotides $p22^{phox}$ (FIG. 4A) and NOX4 (FIG. 4B). Thus, the NAD(P)H oxidase is a normal component of signaling machinery that may be parasitized to serve malignant proliferation.

Figure 2:
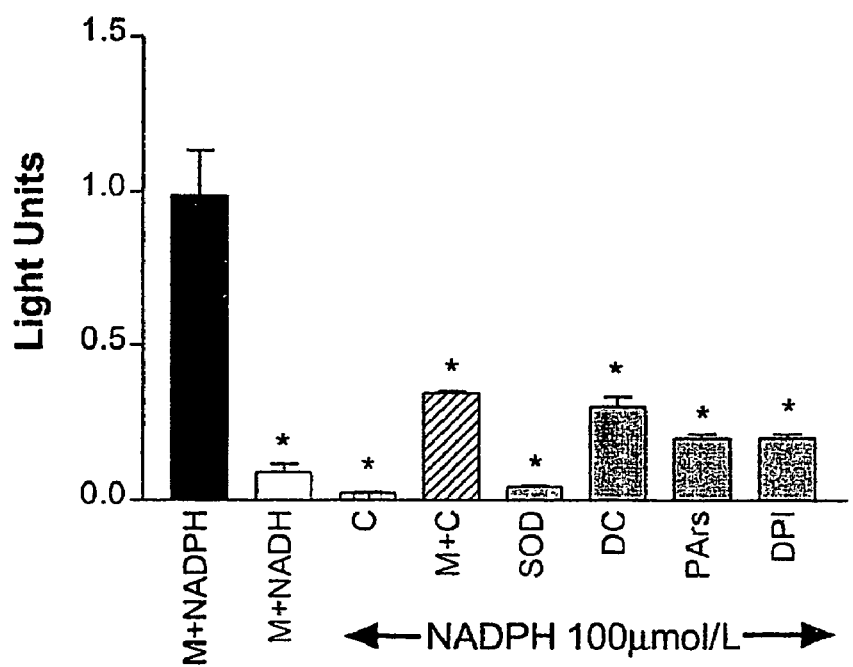
FIG. 2 is a graph showing that plasma membranes from malignant melanoma cells generate reactive oxygen species.

The putative melanoma NAD(P)H oxidase shares some of the functional properties of the NAD(P)H oxidase of phagocytes, but with important differences. Like the phagocyte oxidase, the initial enzyme product appears to be $O_2^-$ (FIG. 2). Also, the melanoma oxidase activity appears to be localized in membranes rather than in the cytosol (FIG. 2). The melanoma oxidase utilizes NADPH as its preferred substrate (FIG. 2). However, in vascular smooth muscle cells, which express $gp91^{phox}$, NOX1 and NOX4, appear to employ only NOX1 as the functional homolog (13. Lassegue et al. (2001) *Circ. Res.* 88:888–894).

In phagocytes, the NAD(P)H oxidase consists of two membrane proteins, $gp91^{phox}$ and $p22^{phox}$ that bind a flavin adenine nucleotide (FAD) and form a cytochrome with a redox midpoint potential of –245 mV and a reduced minus oxidized difference spectrum of 558 (B. M. Babior (1999) *Blood* 93:1464–1476). At least two and possibly three cytosolic proteins ($p47^{phox}$, $p67^{phox}$ and p40) are also essential and several other cytosolic components participate, including the small GTPases, Rac1 or Rac2. The oxidase is thought to contain all the factors necessary for transporting electrons from the donor substrate NADPH via FAD to generate superoxide ($O_2^-$) from molecular $O_2$. A similar oxidase has been reported to serve a signaling function in nonphagocytic cells, where it appears to share some of the components with its phagocyte cousin, but with critical distinctions, including a delayed time course for activation and lower level of activity. Endothelial cells appear to express all the phagocyte oxidase components, including $gp91^{phox}$, $p22^{phox}$, $p47^{phox}$ and $p67^{phox}$ (A. Gorlach et al., supra; S. A. Jones et al., supra). In contrast, vascular smooth muscle cells express $p22^{phox}$ (K. K. Griendling et al., supra; M. Ushio-Fukui et al. (1996) *J. Biol. Chem.* 271:23317–23321), $p47^{phox}$ (K. K. Griendling et al., supra), and the unique homolog NOX1 (B. Banfi et al. (2000) *Science* 287:138–142; B. M. Babior, supra; K. K. Griendling et al., supra; Y-A. Suh et al., supra). Yet another $gp91^{phox}$ homolog NOX4 has been described in renal tubular epithelial cells (M. Geiszt et al. (2000) *Proc. Natl. Acad. Sci. USA,* (2000) 97:8010–8014; A. Shiose et al. (2001) *J. Biol. Chem.* 276:1417–1423), fetal tissue (G. Cheng et al., supra), placenta (G. Cheng et al., supra), and proliferating vascular smooth muscle (B. Lassegue et al., supra).

It has been found that NOX4 in normal human epidermal melanocytes and in malignant melanoma cells, where interference with its expression substantially inhibits malignant proliferation (FIG. 4B). These results differ from experiments in normal cells, where NOX4 transfection suppresses rather than enhances proliferation (M. Geiszt et al., supra; A. Shiose et al., supra). However, the finding of NOM in renal cell carcinomas (A. Shiose et al., supra), glioblastomas (G. Cheng et al., supra) and CaCo colon cancer cells (G. Cheng et al., supra), and now in malignant melanomas, raises the possibility that this unique homolog might play an important redox signaling role necessary for malignant prosperity and progression.

A potentially large number of signal transduction and gene expression systems might be influenced by a growth regulatory NAD(P)H oxidase (B. M. Babior, supra), among which is the redox-regulated transcription factor NF-κB. Brar, et al. have previously shown that antioxidants reduce IκBα phosphorylation and constitutive NF-κB activation in malignant melanoma cells (Brar et al., supra).

It has been shown that the flavoprotein inhibitor diphenylene iodonium reduces IκBα phosphorylation (FIG. 5F) and constitutive NF-κB activation (FIGS. 5A–E), suggesting that reactive oxygen species from an NAD(P)H oxidase contribute to constitutive NF-κB activation.

Repression of NF-κB interferes with normal and transformed cell proliferation (M. Hinz et al. (1999) *Mol. Cell Biol.* 19:2690–2698; B. Kaltschmidt et al. (1999) *Oncogene* 18:3213–32257), and inhibition of NF-κB by antisense strategies (K. A. Higgins et al. (1993) *Proc. Natl. Acad. Sci. USA* 90:9901–9905) or by overexpression of the NF-κB inhibitor IκBα blocks tumor growth. In malignant melanomas NF-κB is activated as a result of enhanced constitutive IκB kinase activity (R L. Shattuck-Brandt et al., supra) and is thought to play a significant role in autocrine generation by melanomas of the chemokines MGSA$_\alpha$/GRO$_\alpha$ and interleukin-8 (J. Yang et al. (2001) *Cancer Res.* 61:4901–4909).

It was observed from the results shown in FIG. 6 that, in contrast to results with other tumor types, growth of M1619 melanoma cells by expression of a superrepressor form of the NF-κB inhibitor IκBα was not suppressed. Thus, NF-κB activation in this melanoma cell line may play a greater role in conferring resistance of the tumor to apoptosis, chemotherapy and radiation through upregulating expression of anti-apoptotic bcl-2 family proteins (A. A. Beg et al. (1996) *Science* 274:782–784; C—Y. Wang et al. (1999) *Nature Med.* 5:412–417).

As shown by the significant inhibition by diphenylene iodonium of DNA binding to CRE (FIGS. 7B and 7C), an alternative group of transcription factors that could be redox-regulated by the NAD(P)H oxidase is the ATF/CREB family (O. M. Andrisani (1999) *Crit. Rev. Eukaryotic Gene Expression* 9:19–32; S-I. Kurata (2000) *J. Biol. Chem.* 275:23413–233416). Molecular disruption of ATF/CREB-mediated transcription has been previously shown to reduce proliferation, metastatic potential and radiation resistance of malignant melanomas (P. M. Cox et al. (1992) *Nucleic Acids Res* 20:4881–4887; Z. Ronai et al. (1998) *Oncogene* 16:523–531; D. Jean et al., supra; S. Xie et al., supra).

Others have previously shown the importance of $O_2^-$ in mitogenic signaling (K. Irani et al, supra; T. Joneson et al, supra), and transfection with NOX1 transforms normal fibroblasts (Y-A. Suh et al., supra) and creates cell lines that are tumorigenic in athymic mice (R. Arnold et al., supra). The exact contribution of autocrine ROS toward the transformed, neoplastic condition is still unclear. However, based upon its strategic role in melanomas and presence in other malignant cell lines (G. Cheng et al., supra; H. Kikuchi et al, supra; A. Shiose et al., supra), a membrane NAD(P)H oxidase may be fundamentally important for growth signaling in a broad array of tumors. If so, NAD(P)H oxidase inhibitors might present a new strategy for cancer therapy, with coumarin analogs offering promise to this end.

It has been found that dicumarol inhibits lucigenin chemiluminescence by melanoma plasma membranes in an in vitro system lacking cytosolic components (FIG. 2), suggesting inhibition of membrane NAD(P)H oxidase activity. Other coumarins have previously been reported to block $O_2^-$ by the neutrophil NADPH oxidase (F. Bertocchi et al. (1989) *Naunyn-Schmiedebergs Archiv. Pharmacol* 339:697–703; M. Paya et al. (1993) *Arzneimittel-Forschung* 43:655–658). Furthermore, prolonged treatment with the coumarin warfarin has been recently shown to reduce subsequent risk of cancer (S. Schulman et al. (2000) *N. Engl. J. Med.* 342: 1953–1958). This beneficial effect of warfarin has been attributed to anticoagulation (S. Schulman et al., supra; C. C. Zielinski et al. (2000) *N. Engl. J. Med.* 342:1991–1993), but an alternative possibility is that certain coumarins inhibit a growth regulatory NAD(P)H oxidase important for malignant cell growth.

The method of this invention uses coumarin or a coumarin analog or derivative or diphenylene iodonium as a medicament comprising a doses of dicumarol in an amount effective to disrupt the performance of the NAD(P)H oxidase and production of its reactive oxygen species signaling products. The medicament doses are from 1 mg. to 500 mg. per day, preferably from about 50 mg to about 200 mg per day. The result of such treatment is the regulation of vascular and other smooth muscle tone, treatment of ischemia-reperfusion injury syndromes such as myocardial infarction and stroke, lowering blood pressure, treatment of asthma and regulation of growth and proliferation of cancer.

The instant medicaments can further comprise the coumarin or coumarin analog in a physiologically acceptable carrier for administration. Any physiologically buffered saline, normal saline and distilled water. By "pharmaceutically acceptable" is meant a material that is not biologically or other wise undesirable, i.e., the material may be administered to an individual orally without causing any undesirable biological effects or interacting in a deleterious manner with any of the other components of the pharmaceutical composition in which it is contained.

The invention further provides that the medicament can be administered in aerosol particles, by inhalation, by intratracheal injection, by intra venous injection, by peritoneal injection. When using an aerosol it has been found particularly useful to combine the medicament with vitamin K to prevent anticoagulant activity. Aerosol particles can consist essentially of particles less than 10 microns and preferably less than 5 microns. Such aerosols can be provided by available jet aerosol or ultrasonic nebulizer systems in common use.

Materials. Human malignant cell lines were obtained from American Type Culture Collection (Rockville, Md.). Human epidermal melanocytes, Medium 154 and Human Melanocyte Growth Supplement (HMGS) were purchased from Cascade Biologics, Inc., Portland, Oreg. RPMI medium 1640, N-2-hydroxyethylpiperazine-N'-2-ethanesulfonic acid (HEPES), antibiotic-antimycotic (10,000 U penicillin, 10,000 μg streptomycin, and 25 μg amphotericinB/ml), and trypsin-ethylenediaminetetraacetic acid (EDTA) solution were purchased from the GIBCO-BRL division of Life Technologies (Grand Island, N.Y.). Fetal bovine serum was purchased from HyClone Laboratories (Logan, Utah). The intracellular oxidant sensitive probe 2',7'-dichlorofluorescin diacetate (DCFH-DA) was from Molecular Probes (Eugene, Oreg.). EMSA supplies were purchased from ProMega (Madison, Wis.). Supershift antibodies were obtained from Santa Cruz Biotechnology, Santa Cruz, Calif. Rabbit phospho-specific antibodies for IκBα phosphorylated at serine 32 were purchased from New England Biolabs (Beverly, MA). Protease inhibitors were from Sigma Chemical Co. (St. Louis, Mo.). All other materials were purchased from Sigma Chemical Co. (St. Louis, Mo.), unless specified.

Culture of malignant cell lines and cell culture treatments. Malignant melanoma cell lines were cultured and passaged as described Brar, et al. (See Brar et al., supra). Human epidermal melanocytes were cultured in Medium 154 supplemented with HMGS according to supplier's instructions and passed with 0.05% trypsin and 0.53 mmol/L EDTA. Growth rates of melanocytes and M1619 melanoma cells were compared by measuring proliferation as described below every 24 hours for 72 hours. Intracellular generation of ROS by melanocytes or M1619 cells was measured by oxidation of 2',7'-dichlorofluorescin diacetate (DCFH-DA) to 2',7'-dichlorofluorescein (DCF) by $H_2O_2$. The effect of NAD(P)H oxidase inhibitors and blockade of the flavoprotein-dependent enzymes xanthine oxidase and nitric oxide synthetase on proliferation of malignant cell lines was studied in cultures stimulated with 10% FBS and grown for 48 hours before measurement of proliferation as detailed below. The effect of NAD(P)H oxidase activity on transcriptional activation was studied by incubation of 70% confluent cultures with 0–50 µmol/L of the flavoprotein inhibitor diphenylene iodonium (DPI) for 24 hours prior to measurement of DNA binding by electrophoretic mobility shift assay (EMSA), constitutive NF-κB nuclear activation by immunohistochemical staining for the p65 component, or immunoassay of levels of active transcription factor component in nuclear protein.

Measurement of proliferation in cell cultures. Proliferation of cultured cells seeded into 24-well uncoated plastic plates (Costar) at 50,000 cells per well (except where indicated) was quantitated as described by Brar et al. (Brar et al., supra) using a colorimetric method based upon metabolic reduction of the soluble yellow tetrazolium dye 3-[4,5,-dimetylthiazol]-2yl-2,5-diphenyl tetrazolium bromide (MTT) to its insoluble purple formazan by the action of mitochondrial succinyl dehydrogenase. For studies with a final cell density of less than about 40,000 cells per well, direct cell counts were performed on 10 random fields/well of Wright's-modified Geimsa stained monolayers viewed at a magnification of 40× using a 0.01 $cm^2$ ocular grid.

Measurement of reactive oxygen species generation by intact cells. Intracellular production of reactive oxygen species by M1619 cells or epidermal melanocytes was measured using oxidation of 2',7'-dichlorofluorescin diacetate (DCFH-DA) to 2',7'-dichlorofluorescein (DCF) (J. A. Royal et al., supra). DCFH-DA is a nonpolar compound that readily diffuses into cells, where it is hydrolyzed to the nonfluorescent polar derivative DCFH and thereby trapped within the cells. In the presence of $H_2O_2$, DCFH is oxidized to the highly fluorescent 2',7'-dichlorofluorescein (DCF). Approximately $1 \times 10^6$ M1619 cells or human epidermal melanocytes were incubated in the dark for 10 minutes at 37° C. with 50 mol/L DCFH-DA, harvested and resuspended in plain media. Fluorescence was analyzed using a FACScan (Becton Dickinson, Sunnyvale, Calif.) flow cytometer with excitation at 488 nm and emission at 530 nm.

Measurement of reactive oxygen species generation by cell membranes. The method of Pagano, et al. (P. J. Pagano et al. (1997) *Proc. Natl. Acad. Sci. USA* 94:14483–14488), with centrifugation speeds modified according to the work of Mohazzab et al. (H. K. M. Mohazzab et al. (1994) *Am. J. Physiol.* 267(*Lung Cell. Mol. Physio.*) 14:L815–L822), was used to prepare membranes for measurement of ROS. M1619 cells from six near confluent T-75 flasks were harvested with Cell Dissociation Solution (Sigma), washed once with ice cold DPBS and centrifuged for 5 minutes at 675 g. The pellet was resuspended in 500 µl of ice cold Tris-sucrose buffer (pH 7.1 comprised of [in mmol/L] Trizma base 10, sucrose 340, PMSF 1, EDTA 1 and 10 µg/ml protease inhibitor cocktail [Sigma]) and sonicated by four 15-second bursts. The cell sonicate was centrifuged at 1,475 g and 4° C. for 15 minutes in an Eppendorf microfuge to remove nuclei and unbroken cells. The supernatant was then centrifuged at 29,000 g and 4° C. for 15 minutes in a Beckman Optima TL ultracentrifuge. The pellet was discarded and the supernatant was further centrifuged at 100,000 g and 4° C. for 75 minutes. The pellet was resuspended in 100 µl Tris-sucrose buffer and stored at −80° C. Supernatant from the last centrifugation was also saved as representative of lactate dehydrogenase containing-soluble elements of cytoplasm (H. K. M. Mohazzab et al., supra). Generation of ROS was measured by SOD-inhibitable lucigenin chemiluminescence, as reported by Pagano et al. (P. J. Pagano et al., supra) in 500 µl of 50 mmol/L phosphate buffer (pH 7.0), containing 1 mmol/L EGTA, 150 mmol/L sucrose, 5 µmol/L lucigenin, 15 µg cell membrane protein, 50 µg cytosolic protein and 100 µmol/L NADH or NADPH as substrate. Chemiluminescence (in arbitrary light units) was measured using a Turner Model 20/20D luminometer (Turner Designs, Sunnyvale, Calif.) at 30 second intervals for 5 minutes with and without addition of 300 U SOD to determine dependence of light generation upon $O_2$ generation. The signal was expressed as the sum of all measurements after subtraction of the buffer blank (A. Shiose et al., supra). DPI (50 µmol/L) and phenylarsine (1 µmol/L) were added to determine dependence of light generation upon flavoprotein- and gp91$^{phox}$ or NOX-containing NADPH oxidase enzymatic activity, respectively.

Reverse transcriptase polymerase chain reaction (RT-PCR) detection of NAD(P)H oxidase components. To probe for presence of p22, gp91, p47 and p67$^{phox}$ components of the putative analog of neutrophil NAD(P)H oxidase, and the newly described gp91$^{phox}$ homologs NOX1 (R. Arnold et al., supra; B. Banfi et al., supra; Y-A. Suh et al., supra) and NOX4 (G. Cheng et al., supra; M. Geiszt et al., supra; B. Lassegue et al, supra; Ashiose et al, supra), semiquantitative RT-PCR was performed as described by Brar et al. (S. S. Brar et al. (1999) *J. Biol. Chem.* 274:200017–200026) on triplicate near confluent cultures of proliferating cells grown in 25-mm plastic dishes. Cell monolayers were washed twice with DPBS and lysed with 4 mol/L guanidine thiocyanate, 25 mmol/L sodium citrate, and 0.5% N-lauroylsarcosine. After scraping, lysates were sheared with four passes through a pipette. RNA was extracted by the phenol-chloroform method (P. Chomczynski et al., (1987) *Anal. Biochem.* 162:56–159) and quantitated spectrophotometrically at 260 and 280 nm. RNA (2 µg) was reverse transcribed using 200 units of M-MLV revere transcriptase (Promega) in a reaction mixture containing 1 mmol/L dATP, dCTP, dGTP, and dTTP; 40 unit of RNase inhibitor; 25 µmol/L random hexamers, 5 mmol/L MgC12, 500 mmol/L KC1, and 100 mmol/L Tris-HCl (pH 8.3), in a total volume of 50 µl. The resultant cDNA was PCR amplified for GAPDH, p22$^{phox}$, gp91$^{phox}$, p47$^{phox}$, p67$^{phox}$, NOX1 and NOX4 using human gene-specific sense and antisense primers based on sequences published in GenBank™:

GAPDH-5' ACCACCATGGAGAAGGCTGG [SEQ ID NO 1];
GAPDH-3' CTCAGTGTAGCCCAGGATGC [SEQ ID NO 2];
p22$^{phox}$-5' ATGGAGCGCTGGGGACAGAAGCACATG [SEQ ID NO 3];
p22$^{phox}$-3' GATGGTGCCTCCGATCTGCGGCCG [SEQ ID NO 4];
gp91$^{phox}$-5' TCAATAATTCTGATCCTTATTCAG [SEQ ID NO 5];
gp91$^{phox}$-3' TGTTCACAAACTGTTATATTATGC [SEQ ID NO 6];
NOXI-5' CTGGGTGGTTAACCACTGGTTT [SEQ ID NO 7];

NOX1-3' GAATCCCTAAGTGCCGTAACCA [SEQ ID NO 8].

NOX4-5' TAACCAAGGGCCAGAGTATCACT [SEQ ID NO 9];

NOX4-3' GGCCCTCCCACCCATAGATT [SEQ ID NO 10];

p47$^{phox}$-5' ACCCAGCCAGCACTATGGGT [SEQ ID NO 11];

p47$^{phox}$-3' AGTAGCCTGTGACGTCGTCT [SEQ ID NO 12];

p67$^{phox}$-5' CGAGGGAACCAGCTGATAGA; [SEQ ID NO 13]; and p67$^{phox}$-3' CATGTGAACACTGAGCTTCA [SEQ ID NO 14].

PCR was carried out on a Perkin-Elmer DNA thermal cycler 480. Except where indicated, amplification was carried out for 30 cycles for GADPH, 32 cycles for p22$^{phox}$, 34 cycles for NOX4 and 36 cycles for all other primers at 95° C. for 1 minute, 58° C. for 1 minute, and 72° C. for 2 minutes, followed by an extension step at 72° C. for 10 minutes. PCR-amplified DNA was separated on 1.2% agarose gel, stained with ethidium bromide, and visualized and photographed under ultraviolet light. PCR products from defined bands were purified with QIA quick gel extraction kits (Qiagen, Chatsworth, Calif.) and sequenced automatically by an ABI Prism 310 Genetic Analyzer (Applied Biosystems, Foster City, Calif.) using the same respective primers for sequencing as for PCR.

Immunoassay for p22$^{phox}$, gp91$^{phox}$, IκBα, phosphorylated IABα and p65 component of NF-κB. To measure protein expression of p22$^{phox}$ and gp91$^{phox}$ in the cytosol and in the 100,000 g plasma membrane fraction of M1619 cells, immunoassays were performed as detailed earlier (S. S. Brar et al., supra) using previously described rabbit polyclonal antibodies prepared against whole human p22$^{phox}$ (R3179) (A. J. Jesaitis et al. (1990) J. Clin. Invest. 85:821–835) and gp91$^{phox}$ C-terminal peptide (82089)(M. T. Quinn et al. (1989) Nature 342:198–200) at dilutions of 1:1,000. To assess nuclear translocation of the cytosolic transcription factor NF-κB, the p65 NF-κB component was similarly immunoassayed in nuclear protein that was isolated as outlined below. For immunoassay of the NF-αB inhibitor IκBα or for IκBα phosphorylated at serine 32, the same procedure was followed as previously reported in Brar et al. (2001), supra) with cells lysed in boiling buffer to which 50 mM dithiothreitol (DTT) had been added as a reducing agent.

Transfection protocol for p22$^{phox}$ and NOX4 sense and antisense treatment of M1619 cells. To transfect antisense oligonucleotides for p22$^{phox}$, M1619 cells were cultured in 6-well plates at a density of 20,000 cells per well and grown in RPMI 1640 containing 10% FBS. After 24 hour wells were washed once with DPBS and 800 µl of RPMI 1640 (serum- and antibiotic-free) was added to each well. Previously reported (S. Lynn et al. (2000) Circ. Res. 86:514–519) p22$^{phox}$, sense (5' -GGTCCTCACCATGGGGCAGATC-3') [SEQ ID NO 15] or antisense (5'-GATCTGCCCCATGGT-GAGGACC-3') [SEQ ID NO 16] oligonucleotides (2 µg) were mixed with 5 µl LIPOFECTACE Reagent (Life Technologies) and 200 µl serum- and antibiotic-free RPMI 1640 at room temperature for 15 minutes. This mixture was then added to each well and cells were incubated at 37° C. After 6 hours the transfection mixture was gently removed and replaced with 2.5 ml of RPMI 1640 containing 10% FBS. Cell were incubated an additional 48 hours before staining with hematoxylin and eosin for photography or quantitation of growth with the MTT assay. M1619 cells were transfected with NOX4 sense (5'-TCGAGGAGGTCCTGTGTCGG-3') [SEQ ID NO 17] or antisense (5'-AGCTCCTCCAGGACA-CAGCC-3') [SEQ ID NO 18] oligonucleotides based on gene-specific unique sequences published in GenBank™ (Accession No. NM 016931). The transfection protocol was identical to that used for p22$^{phox}$ oligonucleotides, except that 10 µl LIPOFECTIN Reagent (Life Technologies) was used instead and cells were photographed using a phase-contrast microscope and a green filter.

Electrophoretic mobility shift assays (EMSAs). To assess DNA binding of NF-κB or the cyclic-AMP response element family of binding proteins, nuclear protein was isolated and EMSAs were performed as previously reported (Brar, et al., supra). The consensus binding oligonucleotides, 5'-AGT-TGAGGGGACTTTCCCAGGC-3' [SEQ ID NO 19] and 3'-TCAACTCCCCTGAAAGGGTCCG-5' [SEQ ID NO 20], for the p50 component of NF-κB, 5'-AGAGATTGC-CTGACGTCAGAGAGCTAG-3' [SEQ ID NO 21] and 3'-TCTCTAACGGACTGCAGTCTCTCGATC-5' [SEQ ID NO 22] for the cyclic-AMP response element CRE, and 5'-CGCTTGATGAGTCAGCCGGAA-3' [SEQ ID NO 23] and 3'-GCGAACTACTCAGTCGGCCTT-5 [SEQ ID NO 24] for AP-1, and 5'-TGTCGAATGCAAATCACTAGAA-3', [SEQ ID NO 25] and 3'-ACAGCTTACGTTTAGT-GATCTT-5' [SEQ ID NO 26] for OCT1 were used in binding reactions after end-labeling by phosphorylation with [γ$^{32}$P]-ATP and T4 polynucleotide kinase. Competition experiments were performed with 10X respective unlabeled wild-type oligonucleotide sequences, and supershift experiments were carried out by incubating the binding reaction with 1 µg of supershift antibody.

Immunohistochemical localization of NF-κB. Constitutive activation of NF-κB was also studied by qualitatively assessing nuclear localization of the p65 component by immunohistochemical staining, as described (Brar et al., supra).

Transduction protocols for IκBα gene transfer. To repress activation of NF-κB, cells were transduced with adenoviral (Ad serotype 5; Ad5) vectors that were E1a/E1b-deleted and expressed a superrepressor of NF-κB (AdI$_κ$B$_α$SR, 2×10$^{11}$ plaque forming units/ml) under the regulation of the cytomegalovirus (CMV) immediate-early promoter region (R. K. Batra et al. (1999) Am. J. Respir. Cell. Mol. Biol. 21:238–245) or expressed the CMV immediate-early promoter region alone (AdCMV-3, 2.05×10$^{11}$ plaque forming units/ml, control vector). These Ad vectors were constructed in the Vector Core Laboratory at the Gene Therapy Center of the University of North Carolina School of Medicine and were generous gifts, respectively, from Dr. A. S. Baldwin of the Lineberger Cancer Center and Dr. A. Ghio of the U.S. EPA Human Health Effects Center, Chapel Hill, N.C. Transduction was performed using previously published protocols (R. K. Batra et al., supra). M1619 cells were seeded onto 24-well plates at a density of 25,000 cells/well and grown for 6 hours in RPMI 1640 with 10% FBS. Media was removed and replaced with 200 µl complete medium containing approximately 1.25×10$^6$ to 2.0×10$^7$ colony forming units of AdIκBαSR or AdCMV-3. After overnight incubation, the vector containing media was removed, and cells were washed once with warm DPBS and reincubated with fresh complete media After an additional 24 hour, proliferation was assessed with the MTT assay.

Statistical analysis. Data are expressed as mean values±standard error for a minimum number of four observations, unless indicated. Differences between two groups were compared using the unpaired Student's t test. Two-tailed tests of significance were employed. Differences between multiple groups were compared using one-way analysis of variance. The post-hoc test used was the Newman-Keuls multiple comparison test. Significance was assumed at p<0.05.

The present invention is more particularly described in the following examples which are intended as illustrative only, since numerous modifications and variations therein will be apparent to those skilled in the art.

EXAMPLE 1

Malignant Melanonza Cells Produce Intracellular Reactive Oxygen Species.

Intracellular production of reactive oxygen species by M1619 cells was measured using oxidation of 2', T-dichlorofluorescin diacetate (DCFH-DA) to 2', 7'-dichlorofluorescein (DCF) (J. A. Royall et al. (1993) Archiv. Biochem. Biophys. 302:348–355). DCFH-DA is a nonpolar compound that readily diffuses into cells, where it is hydrolyzed to the nonfluorescent polar derivative DCFH and thereby trapped within the cells. In the presence of $H_2O_2$, DCFH is oxidized to the highly fluorescent 2',7'-dichlorofluorescein (DCF). Approximately $1 \times 10^6$ M1619 cells were incubated in the dark for 10 minutes at 37° C. with 50 µmol/L DCFH-DA, harvested and resuspended in plain media. Fluorescence was analyzed in approximately 10,000 cells each using a FACScan (Becton Dickinson, Sunnyvale, Calif.) flow cytometer with excitation at 488 rim and emission at 530 nm.

Figure 1:
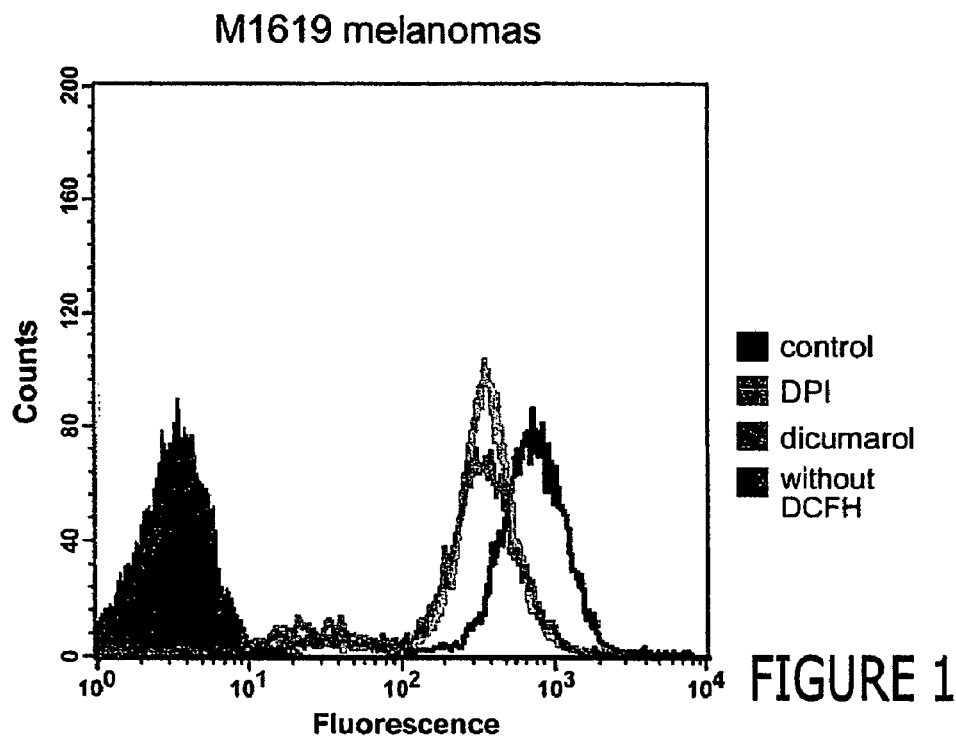
FIG. 1 shows that the generation of intracellular reactive oxygen species in melanomas is inhibited by diphenylene iodonium and dicumarol.

FIG. 1 shows a comparison to spontaneous fluorescence of cells without DCFH treatment (blue-shaded areas) wherein M1619 melanoma cells oxidized DCFH to DCF. Pretreatment of cells for 15 minutes with diphenylene iodonium (DPI; 50 µmol/L) or dicumarol (250 µmol/L) reduced DCFH oxidation to DCF. Treatment with DPI or dicumarol in the absence of DCFH did not result in significant cellular fluorescence within the monitored spectrum (data not shown). Mean fluorescence=754 untreated, 408 DPI, 396 dicumarol; median fluorescence 685 untreated, 355 DPI, 359 dicumarol.

These results show that during proliferation, melanomas and melanocytes produce intracellular reactive oxygen species, oxidant generation is blocked by DPI and dicumarol, and growth is disrupted by antioxidant strategies.

EXAMPLE 2

Malignant Melanoma Cell Membranes Produce Reactive Oxygen Species.

In this example the source of $O_2^-$ generation was studied by preparing plasma membrane and cytosolic fractions from proliferating M1619 melanoma cells. The plasma membrane and cytosolic fractions were examined for their respective abilities to support SOD-inhibitable lucigenin chemiluminescence.

The 100,000 g membrane fraction of proliferating M1619 melanoma cells was prepared as described above. Chemiluminescence stimulated by 15 gg membrane protein was measured after incubation for 5 minutes in the presence of 5 µmol/L lucigenin and 100 µmol/L NADH or NADPH, with and without addition of 50 µg cytosolic protein, 300 units/ml SOD, 50 µmol/L diphenylene iodonium (DPI), 1 µmol/L phenylarsine oxide or 50 µmol/L dicumarol. M=membrane; C= cytosol; M+C=membrane+cytosol; SOD=membrane+SOD; DC=membrane+dicumarol; PArs=membrane+phenylarsine oxide; DPI=membrane+DPI; n=4 for each observation; *P<0.001 vs membranes+NADPH.

As shown in FIG. 2 plasma membranes alone significantly increased SOD-inhibitable lucigerin chemiluminescence, without addition of cell cytosol. When lucigenin was used at a concentration of 5 µmol/L to prevent artifactual redox cycling, the preferred substrate for generation of $O_2^-$ was NADPH rather than NADH (column 1 vs 2). Cytosol from M1619 cells did not support chemiluminescence (column 4), mitigating against the cytosolic enzyme NQO1 as the source driving $O_2^-$ generation in this cell line. Also, addition of cytosol to membranes and NADPH did not increase light emission. Chemiluminescene was significantly inhibited by SOD, and by addition of the NADPH oxidase inhibitor phenylarsine oxide and the flavoprotein inhibitor diphenylene iodonium (DPI).

These results show that light emission is the result of $O_2^-$ generated by a membrane NAD(P)H oxidase. Both phenylarsine oxide (at 10–50 µmol/L) and DPI (at 10–50 µmol/L) also significantly inhibited M1619 malignant melanoma cell growth (96.2±0.6% and 86.0±0.5 inhibition after 48 hours, respectively, at the highest dose of each; P<0.001), but melanoma growth was unaffected (data not shown) by inhibitors of the other flavoprotein oxidases xanthine oxidase (allopurinol, 1 mmol/L) or nitric oxide synthetase (ω-nitro-L-arginine, 100 µmol/L). Chemiluminescence generation was likewise reduced by direct addition of dicumarol to the membrane preparation, in the absence of cytosol. These results show that dicumarol inhibits plasma membrane NAD(P)H oxidase activity.

EXAMPLE 3

Malignant Melanoma Cells and Melanocytes Express NAD(P)H Oxidase Components that are Necessary for Proliferation.

To determine whether components of the NAD(P)H oxidase-neutrophil-or its homologs are also expressed in melanomas and non-malignant melanocytes, RT-PCR on RNA extracted from proliferating cells stimulated by 10% FBS (melanomas) or HMGS (melanocytes) were performed and the results shown in FIG. 3.

In FIG. 3A the gels represent RT-PCR at 36 cycles. M1619 melanoma cells (FIG. 3A, top panel, lane 2) and other malignant melanomas (Table 1) strongly expressed the alpha subunit of cytochrome $b_{558}$, $p22^{phox}$, initially detected at 32 cycles. The 252 base pair PCR product obtained has been sequenced and is identical to bases 221–372 of the reported human mRNA sequence (Accession No. XM 008040).

Proliferating human melanoma cells also expressed $gp91^{phox}$ (top panel, lane 3, and Table 1 detectable only after 36 cycles as a 557 base pair product that was sequenced and found corresponding to bases 630 to 1158 of the reported human mRNA sequence; Accession No. NM 000397). Normal melanocytes expressed $p22^{phox}$ but not $gp91^{phox}$. Surprisingly, M1619 melanoma cells strongly and melanocytes modestly expressed the $gp91^{phox}$ homolog NOX4 (top and second panels, lane 7), detected using the primers NOX4-5' TAACCAAGGGCCAGAGTATCACT; NOX4-3' GGCCCTCCCACCCATAGATT [SEQ ID NO 10]. The 564 base-pair product corresponded to sequences corresponding to bases 197 to 741 of the reported human mRNA sequence (Accession No. 016931). No NOX1 homolog was found in either melanomas or melanocytes (lane 6, 36 cycles). The $p67^{phox}$ cytosolic component was also detected in melanomas (top panel, lane 5, 36 cycles, 727 base pairs, with sequences identical from bases 556 to 1283 of the reported human mRNA sequence; Accession No. BC 001606), and faint PCR product was found in melanomas for p47$^{phox}$ (top panel, lane 4, 36 cycles). GAPDH is shown in lane 1. PCR products were compared to that from an equal amount of mRNA from human PMNs (third panel, for p22$^{phox}$, gp91$^{phox}$, p67$^{phox}$ and p47$^{phox}$) or CaCo colon carcinoma cells (bottom panel, for NOX1 and NOX4), respectively, as shown. RT-PCR was performed using human gene-specific sense and antisense primers based on sequences and conducted as detailed in the text and in Table 1.

Figure 3B:
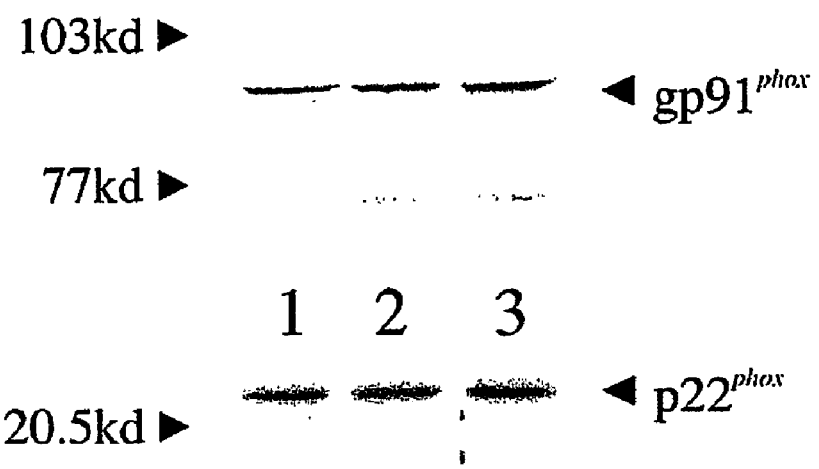
FIG. 3B shows immunoassays of M1619 cells for $p22^{phox}$ and $gp91^{phox}$.

By immunoassay, both p22$^{phox}$, and gp91$^{phox}$ were easily detectable in the 100,000 g plasma membrane fraction of M1619 melanoma cells (FIG. 3B). No evidence was found for the NOX1 homolog of gp91$^{phox}$ (FIG. 3A, top panel, lane 6). However, NOX4 was easily detectable at 34 cycles in M1619 and other malignant melanoma cells (FIG. 3A, top panel, lane 7, and 3C, lanes 1–5) as a 564 base-pair product, with sequences corresponding to bases 197 to 741 of the reported human mRNA sequence. (Accession No. NM 016931).

Melanocytes also expressed p22$^{phox}$ (FIG. 3A, second panel, lane 2) and NOX4 (FIG. 3A, second panel, lane 7), but did not contain mRNA for gp91$^{phox}$ (FIG. 3A, second panel, lane 3). The p67$^{phox}$ cytosolic component was observed in M1619 cells (FIG. 3A, top panel, lane 5; 747 base pairs, with sequences identical from bases 556 to 1283 of the reported human mRNA sequence; Accession No. BC 001606) and two other malignant melanoma cell lines (Table 1). Faint PCR product was also detected in M1619 cells for the p47$^{phox}$ cytosolic component of the leukocyte NADPH oxidase (FIG. 3A, top panel, lane 4), but this product was not sufficiently well-expressed to be sequenced. Neither p67$^{phox}$ nor p47$^{phox}$ were found in epidermal melanocytes. Thus, three known membrane components (p22$^{phox}$ and two possible partners gp91$^{phox}$ and NOX4) and the p67$^{phox}$ cytosolic component of the NAD(P)H oxidase are present in proliferating M1619 and other melanoma cells, and p47$^{phox}$ may be expressed at low levels. In contrast, when proliferating, normal melanocytes express only p22$^{phox}$ and NOX4.

In FIG. 3B the immunoassays of M1619 cells demonstrated that the 100,000 g membrane fraction from triplicate preparations was full size p22$^{phox}$ and gp91$^{phox}$. A second lighter band was seen in immunoassays for gp91$^{phox}$ that may represent unglycosylated protein. In FIG. 3C shows malignant melanoma cells expressing NOX4. RT-PCR was performed for 34 cycles using the gene-specific primers as used above. NOX4 was strongly expressed in the malignant melanoma cell lines M1619 (lane 1), M1585 (lane 2), RLW1495 (lane 3), CMC 9212 (lane 4) and RLW 537 (lane 5).

To begin probing the role of individual NAD(P)H oxidase components in melanoma proliferation, sense and antisense oligonucleotides for p22$^{phox}$ mRNA were transfected into growing M1619 cells. A wide range of commercially available transfection reagents all produced some toxicity to the cells, including the transfection reagents that were ultimately employed. Nevertheless, M1619 cells treated with p22$^{phox}$ antisense oligonucleotides had significantly slower growth subsequent to treatment than did identical cells transfected with sense oligonucleotides for p22$^{phox}$ (FIG. 4A). Thus, p22$^{phox}$ and NOX4 appear to play roles in growth signaling for this melanoma cell line.

The results are shown in FIG. 4A wherein antisense oligonucleotides for p22$^{phox}$ block melanoma growth. M1619 cells (20,000 cells per well) were seeded into 6-well plastic plates and grown for 24 hours. Oligonucleotides were transfected into cells using Lipofectase®, as detailed above. After 6 hours of exposure, transfection solution was replaced with complete media and cells were grown an additional 48 hours. Proliferation was measured by the MTT assay in triplicate experiments. Compared with sense oligonucleotides, treatment with p22$^{phox}$ antisense oliogonucleotides significantly reduced subsequent growth (* P<0.01 vs respective sense oligonucleotides). Hematoxylin- and eosin-stained M1619 cells treated with sense (top) or antisense (bottom) oligonucleotides for p22$^{phox}$ are shown at right. As did several other transfection reagents, Lipofectase® alone also inhibited proliferation compared to untreated cells (55 f 4% for Lipofectase; P<0.01).

Melanoma cells transfected with NOX4 antisense oligonucleotides, with the exception that Lipofectin® was used. These cells also had significantly slower growth subsequent to treatment than did cells transfected with sense oligonucleotides for NOX4 (FIG. 4B). Compared with sense oligonucleotides, treatment with NOX4 antisense oliogonucleotides significantly reduced subsequent growth (*P<0.01 vs respective sense oligonucleotides). Phase contrast micrographs are shown at right of p. cells treated with sense (top) or antisense (bottom) oligonucleotides for NOX4. As did Lipofectase® or Lipofectin® alone also inhibited proliferation compared to untreated cells (21 f 1% for Lipofectin; P<0.01).

Using the same primers expression of p22$^{phox}$, gp91$^{phox}$ and occasionally p67$^{phox}$ by other malignant cell lines was detected, including small cell and non-small cell lung cancers, and ovarian, breast and prostate adenocarcinomas (Table 1). Prostate LnCap carcinoma expressed the NOX1 homolog. H82 small cell carcinoma strongly and H520 squamous cell lung cancer weakly expressed NOX4 (data not shown).

RT-PCR was performed using human gene-specific sense and antisense primers based on sequences published in GenBank™ as shown by [SEQ ID NO 1] through [SEQ ID NO 14]. PCR was carried out for 30 cycles for GAPDH, 32 cycles for p22$^{phox}$ and 36 cycles for all other primers, with amplification at 95° C. for 1 minute, 58° C. for 1 minute, and 72° C. for 2 minutes, followed by an extension step at 72° C. for 10 minute. PCR-amplified DNA was separated on 1.2% agarose gel, stained with ethidium bromide, and visualized and photographed under ultraviolet light. The results are shown in Table 1.

TABLE 1

RT-PCR EXPRESSION OF NAD(P)H OXIDASE
COMPONENTS IN HUMAN NORMAL AND MALIGNANT CELL LINES

|  | GAPDH | p22 | gp91 | p47 | p67 | NOX1 | Growth |
|---|---|---|---|---|---|---|---|
| Number of PCR Cycles | 30 | 32 | 36 | 36 | 36 | 36 | |
| Size of PCR Product | 528 bp | 252 bp | 527 bp | 727 bp | 747 bp | 663 bp | |
| Human neutrophils | + | + | + | + | + | − | |

TABLE 1-continued

RT-PCR EXPRESSION OF NAD(P)H OXIDASE
COMPONENTS IN HUMAN NORMAL AND MALIGNANT CELL LINES

|  | GAPDH | p22 | gp91 | p47 | p67 | NOX1 | Growth |
|---|---|---|---|---|---|---|---|
| Malignant Melanomas |  |  |  |  |  |  |  |
| M1585 | + | − | + | − | + | − | Slow |
| CMC 9515 | + | + | +/low | − | − | − | Intermediate |
| CMC 9601 | + | + | +/low | − | − | − | Intermediate |
| CMC 9703 | + | + | +/low | − | − | − | Intermediate |
| CMC 9710 | + | + | +/low | − | − | − | Intermediate |
| CMC 9128 | + | + | +/low | − | − | − | Intermediate |
| CMC 0040 | + | + | +/high | − | + | − | Fast |
| CMC 0056 | + | + | +/high | − | − | − | Fast |
| RLW 836 | + | + | +/high | − | − | − | Intermediate |
| RLW 1379 | + | + | +/high | − | − | − | Fast |
| RLW 1402 | + | + | +/low | − | − | − | Intermediate |
| RLW 1495 | + | + | +/low | − | − | − | Intermediate |
| Ovarian carcinoma | + | + | +/high | − | − | − | Intermediate |
| Breast MDA-MB-453 | + | + | variable | − | − | − | Intermediate |
| Prostate LnCap carcinoma | + | − | − | +/low | − | + | Slow |
| Prostate PC3 carcinoma | + | + | +/high | +/low | − | − | Slow |
| Prostate DU145 carcinoma | + | + | +/high | +/low | − | − | Slow |
| Small cell lung H82 cancer | + | + | +/high | +/low | − | − | Intermediate |
| Squamous lung H520 cancer | + | + | +/high | +/low | + | − | Slow |
| Adenosquamous lung H596 cancer | + | + | +/high | +/low | + | − | Intermediate |

EXAMPLE 4

NF-κB is Constitutively Expressed in Melanoma Cells and may be Regulated by the NAD(P)H Oxidase.

Figure 5A:
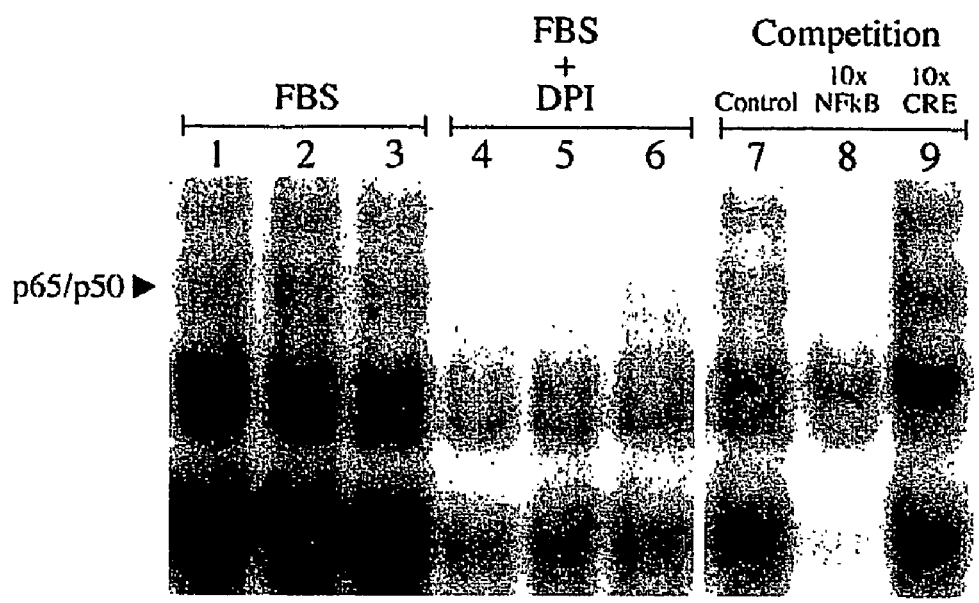
FIG. 5A shows that the flavoprotein-dependent NAD(P)H oxidase inhibitor diphenylene iodonium decreases NF-κB DNA binding.
Figure 5B:
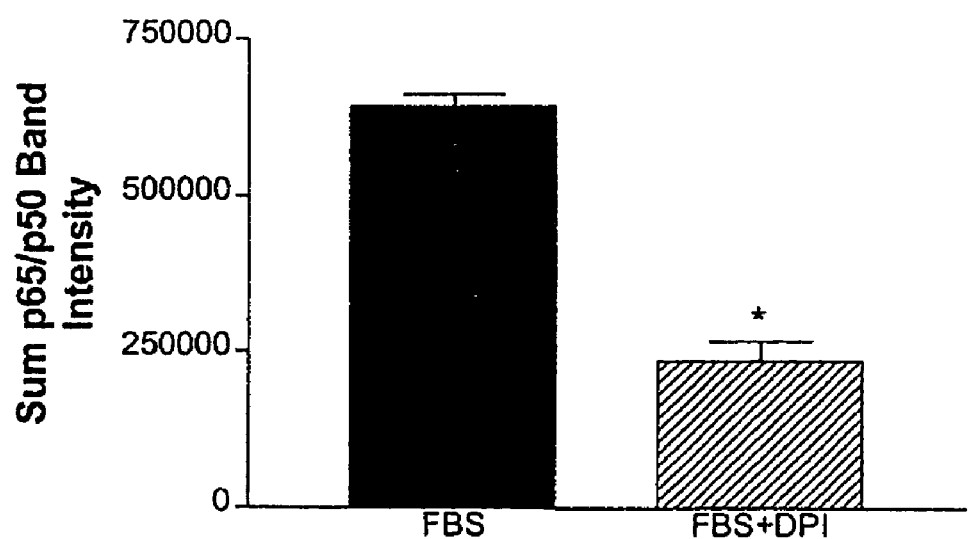
FIG. 5B shows densitometry results of the p65–p50-containing bands from gels in FIG. 5A.
Figure 5C:
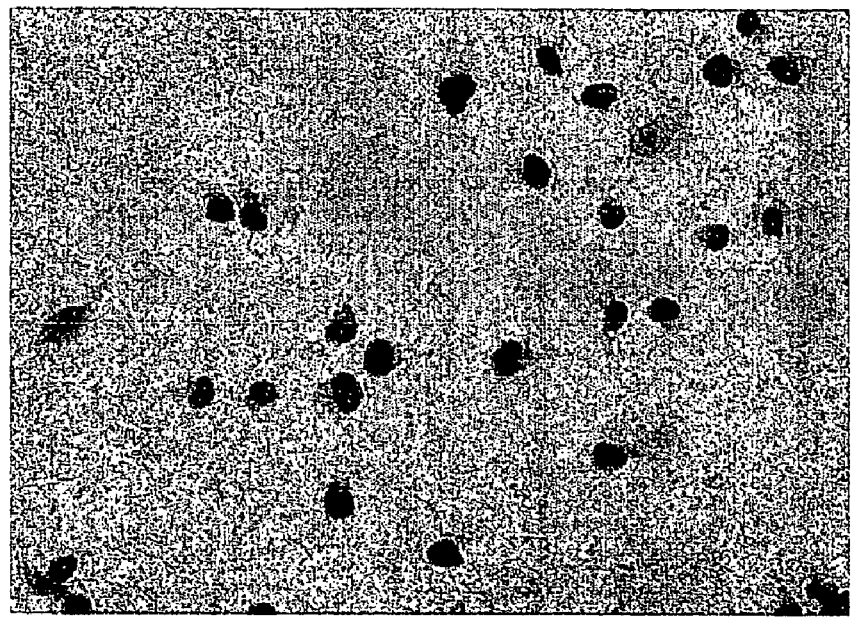
FIG. 5C shows constitutive nuclear translocation of NF-κB is demonstrated in M1619 cells by intense brown immunohistochemical staining for p65 in nuclei.
Figure 5D:
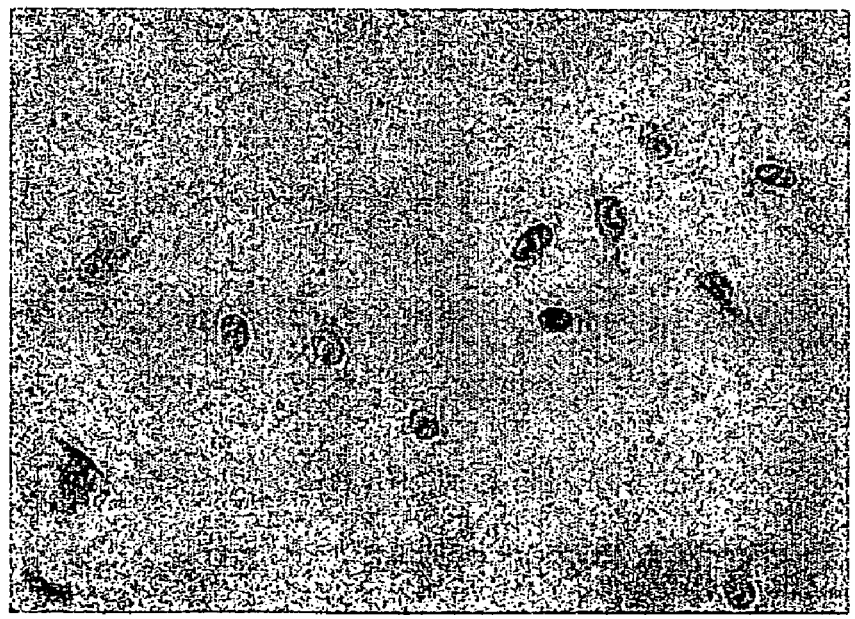
FIG. 5D shows diphenylene iodonium (50 μmol/L overnight) reduces constitutive nuclear translocation of NF-κB.
Figure 5E:
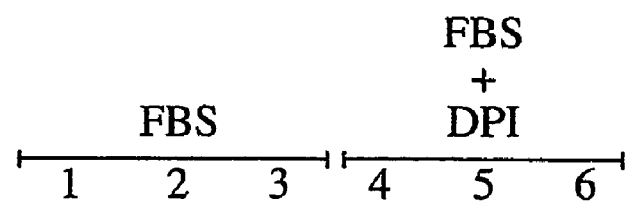
FIG. 5E shows that diphenylene iodonium reduces immunoreactive p65 in nuclear protein.

The flavoprotein-dependent NAD(P)H oxidase inhibitor DPI reduced constitutive activation of NF-κB in melanoma cells, studied by NF-κB DNA binding activity (FIGS. 5A and B), immunohistochemically detectable p65 in nuclei (FIG. 5C vs FIG. 5D) and immunoassay of the p65 NF-κB component in nuclear protein (FIG. 5E).

As shown in FIG. 5A the flavoprotein-dependent NAD(P)H oxidase inhibitor diphenylene iodonium (DPI) decreases NF-κB DNA binding. Near confluent (70%) cultures of M1619 cells (n=3 per group) were incubated overnight with or without 50 μmol/L DPI. Cells were then lysed, nuclear protein was isolated, and EMSAs using $^{32}$p-labeled NF-κB consensus oligonucleotides. The arrow shows the p65/p50-containing dimer. Constitutive NF-κB DNA binding of melanoma cells was greatly reduced in DPI-treated cells (lanes 4–6), compared with cells incubated in growth medium alone (lanes 1–3). In FIG. 5B the densitometry results of the p65–p50-containing bands from gels in FIG. 5A is shown. *P<0.001 compared with no DPI.

In FIG. 5C constitutive nuclear translocation of NF-κB is demonstrated in M1619 cells by intense brown immunohistochemical staining for p65 in nuclei. Confluent cells were fixed in paraformaldehyde, permeabilized, stained using an antibody to the p65 component of NF-κB and a streptavidin-biotin-immunoperoxidase based method outlined in the text, viewed under light microscopy using a blue filter to enhance contrast, and photographed at x400 magnification. FIG. 5D illustrates that DPI (50 μmol/L overnight) reduces constitutive nuclear translocation of NF-κB. Compared with the intense brown nuclear staining for p65 seen in FIG. 5C, DPI-treated M1619 cells demonstrate little anti-p65 brown staining in nuclei. Nucleoli are recognizable in DPI-treated cells (FIG. 5D) but are only occasionally visible in untreated control cells (FIG. 5C).

Figure 5F:
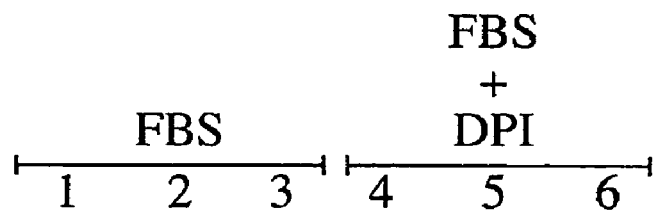
FIG. 5F shows diphenylene iodonium inhibits phosphorylation of the NF-κB inhibitor IκBα.

FIG. 5E demonstrates that DPI reduces immunoreactive p65 in nuclear protein. Near confluent (75%) cultures of M1619 cells (n=3 per group) were incubated overnight with (lanes 4–6) or without (lanes 1–3) 50 μmol/L DPI. Nuclear protein was isolated and immunoassays were performed for the p65 component of NF-κB. DPI treatment of melanoma cells also decreased phosphorylation of the NF-κB inhibitor IκBα (FIG. 5F). Near confluent (75%) cultures of M1619 cells (n=3 per group) were incubated overnight with (lanes 4–6) or without (lanes 1–3) 25 μmoles/L DPI. Cells were lysed and immunoassays were performed using a phospho-specific antibody for IκBα phosphorylated at serine 32.

These findings suggest that a flavoprotein-containing NAD(P)H oxidase may play a role in stimulating constitutive NF-κB transcriptional activity in these cells through generation of ROS.

EXAMPLE 5

Inhibition of NF-κB does not Impair Melanoma Proliferation.

Inhibition of NF-κB by antisense strategies reduces tumorigenicity of fibrosarcomas (K. A. Higgins et al., supra.), and overexpression of the NF-κB inhibitor IκBα blocks tumor cell growth of Hodgkin's disease (R. C. Bargou et al. (1997) *J. Clin. Invest.* 100:2961–2969), squamous cell lung cancer (R. K. Batra et al., supra), squamous cell head and neck cancer (D. C. Duffey et al. (1999) *Cancer Res.* 59:3468–3474) and breast cancer cells. (M. A. Sovak et al. (1997) *J. Clin. Invest.* 100:2952–2960).

Figure 6A:
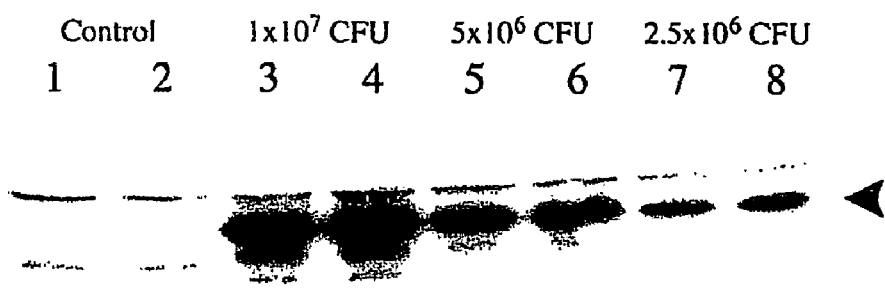
FIG. 6A shows that immunoassays of control M1619 cells or cells transduced with the adenoviral-linked superrepressor form of IκBα (AdIκBαSR).
Figure 6B:
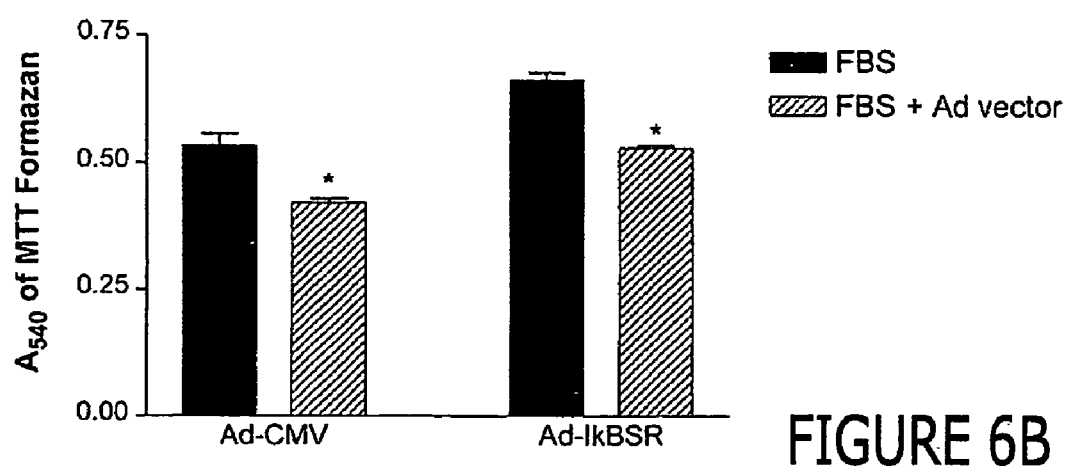
FIG. 6B shows tranduction with IκBαSR does not impair melanoma proliferation.

M1619 cells were infected with an adenoviral vector encoding a superrepressor version of the NF-κB inhibitor IκBα (AdIκBαSR) to determine if selectively inhibiting NF-κB could reduce M1619 melanoma cell proliferation. Cells were grown to near confluence on 25-mm Petri dishes, then transduced with $2.5 \times 10^6$ to $1.0 \times 10^7$ colony forming units (CFU) of AdIκBαSR. After 24 hours, cells were lysed and immunoblots were performed for IκBα. The IκBαSR form of IκBα is seen as a band (arrow) slightly heavier than native IκBα. The results of infection with AdIκBαSR resulted in dose-related increases IκBαSR expression are shown in FIG. 6A.

However, infection with even the highest dose ($1 \times 10^7$ colony forming units) of AdIκBαSR did not substantially reduce M1619 melanoma proliferation (FIG. 6B), especially compared to the profound growth inhibitory effect shown by antioxidants and NAD(P)H oxidase inhibitors in FIG. 1. M1619 melanoma cells were seeded onto 24-well plates at a density of 25,000 cells/well and grown for 6 hours in RPMI 1640 and 10% FBS. Media was removed and replaced with 200 μl complete medium containing $1 \times 10^7$ colony forming units of the adenoviral-linked superrepressor form of IκBα (AdIκBαSR) or the adenoviral vector linked to the CMV promoter (AdCMV-3). After overnight incubation, the vector containing media was removed, and cells were washed once with warm DPBS and reincubated with fresh complete media. After an additional 24 hours, proliferation was quantitated with the MTT assay. Both AdIκBαSR and AdCMV-3 slightly reduced proliferation, but neither had the profound inhibitory effect shown by antioxidants or NAD (P)H oxidase inhibitors in FIG. 1. *P<0.05 vs FBS FIG. 7. NAD(P)H oxidase inhibition reduces DNA binding to the cyclic-AMP responsive element (CRE) but not to AP-1 or OCT-1.

The results show that oxidant generation by a growth regulatory NAD(P)H oxidase regulates proliferation through other signal transduction pathways.

EXAMPLE 6

Inhibition of NAD(P)H Oxidase in Melanoma Cells Reduces DNA Binding Activity for the Cyclic-AMP Response Element (CRE).

Another family of redox responsive transcription factors important for melanoma proliferation are ATF/CREB proteins that bind the cyclic-AMP response element (CRE). The transcription factor CREB (for CRE-binding protein) and its associated family member ATF-1 promote tumor growth, metastases and survival through CRE-dependent gene expression (S. Zie et al., supra), and expression of the dominant negative KCREB construct in melanoma cells decreases their tumorigenicity and metastatic potential in nude mice (D. Jean et al. (1998) *J. Biol. Chem.* 273: 24884–24890).

Figure 7A:
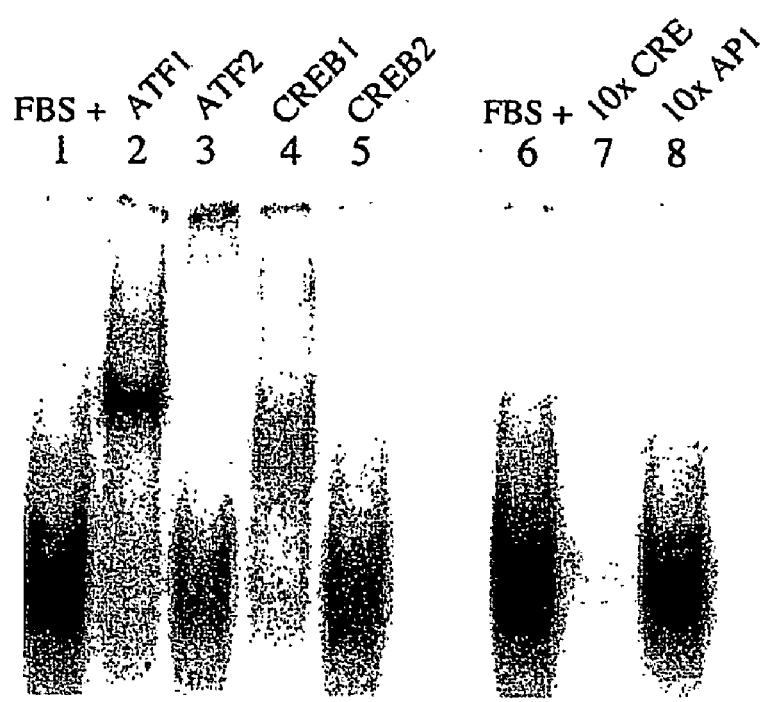
FIG. 7A shows that proliferating M1619 melanoma cells display prominent DNA binding activity (lanes 1 and 6) for the cyclic-AMP responsive element (CRE).

The inhibition of NAD(P)H oxidase in melanoma cells was explored to determine if DNA binding of transcription factors to CRE was reduced. As reported previously for the McWo melanoma cell line (D. Jean et al., supra; S. Xie et al., supra), proliferating M1619 cells displayed prominent DNA binding activity for CRE, comprised of ATF-1, ATF-2 and CREB-1 transcription factors. Supershift experiments with specific antibodies demonstrate that the CREB (for CRE binding protein) family members ATF-1 (lane 2), ATF-2 (lane 3) and CREB-1 (lane 4) contribute to DNA binding activity for CRE. A competition experiment is shown at right, in which addition of 10X molar excess unlabeled CRE (lane 7) but not AP-1 (lane 8) eliminates DNA binding activity for CRE in melanoma nuclear protein. The results in FIG. 7A show that proliferating M1619 melanoma cells display prominent DNA binding activity (lanes 1 and 6) for the cyclic-AMP responsive element (CRE).

Figure 7B:
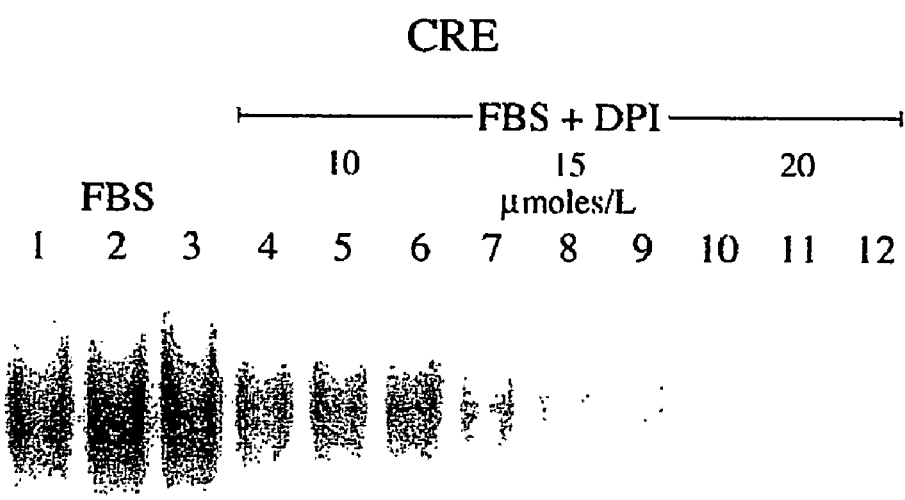
FIG. 7B shows diphenylene iodonium inhibits CRE DNA binding activity in M1619 cells in a dose-dependent manner.
Figure 7C:
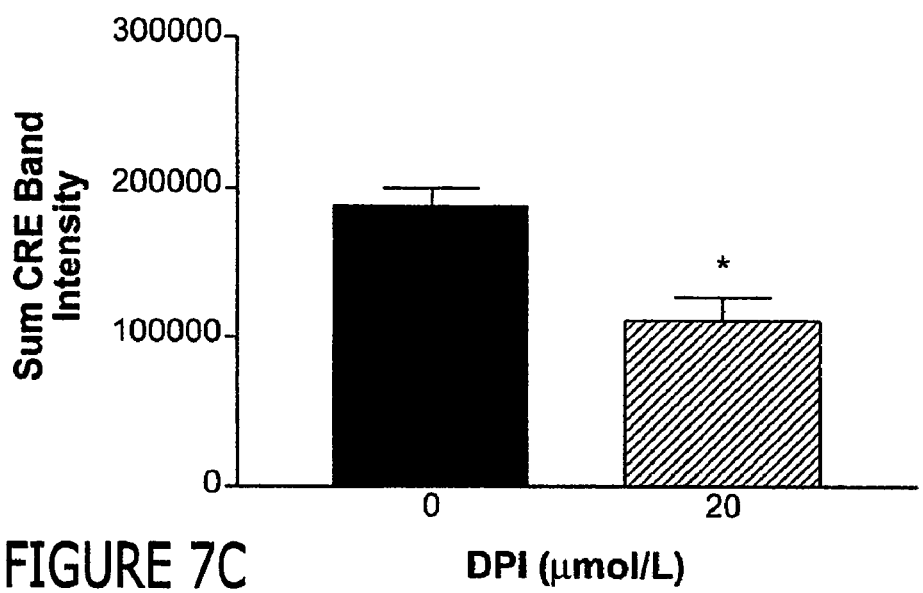
FIG. 7C shows densitometry results of EMSAs shown in FIG. 7B.
Figure 7D:
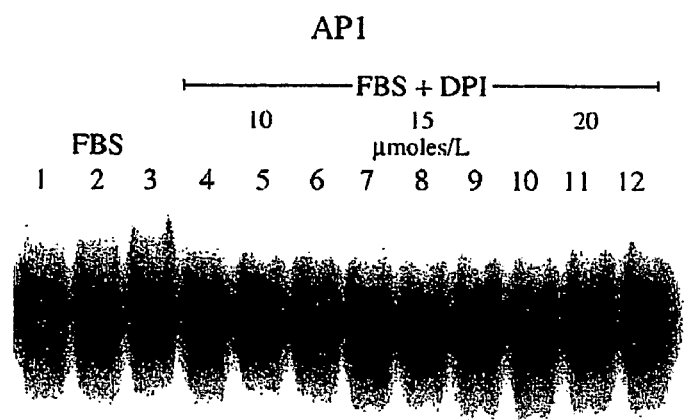
FIG. 7D shows DPI treatment of M1619 cells does not inhibit DNA binding to the AP-1 oligonucleotide consensus sequence.
Figure 7E:
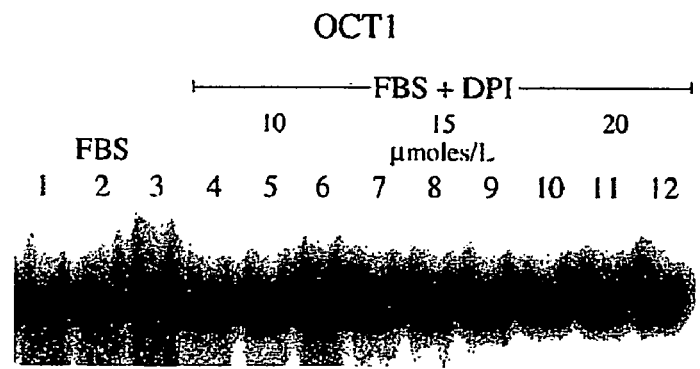
FIG. 7E shows diphenylene iodonium treatment of M1619 cells does not inhibit DNA binding to the OCT-1 oligonucleotide consensus sequence.

Treatment of proliferating M1619 cells overnight with DPI inhibits CRE-binding activity in a dose-dependent manner (FIGS. 7B and 7C), but does not change DNA binding activity of nuclear protein for the transcription factors AP-1 (FIG. 7D) or OCT-1 (FIG. 7E). Near confluent cultures of M1619 cells were treated overnight with DPI, and nuclear protein was harvested for EMSAs. Compared to that in untreated cells (lanes 1–3), treatment with DPI inhibits DNA binding of nuclear protein to CRE in a dose-dependent manner (lanes 4–6, 10 μmoles/L; lanes 7–9, 15 μmoles/L; lanes 10–12, 20 μmoles/L). The results in FIG. 7B show that DPI inhibits CRE DNA binding activity in M1619 cells in a dose-dependent manner. In FIG. 7C the densitometry results of EMSAs of FIG. 7B are shown. *P<0.001 vs untreated cells.

In FIG. 7D the results show that DPI treatment of M1619 cells does not inhibit DNA binding to the AP-1 oligonucleotide consensus sequence. Untreated cells, lanes 1–3; cells treated with 10 μmoles/L, lanes 4–6; cells treated with 15 moles/L, lanes 7–9; cells treated with 20 μmoles/L, lanes 10–12. In FIG. 7E the results show that DPI treatment of M1619 cells does not inhibit DNA binding to the OCT-1 oligonucleotide consensus sequence. Untreated cells, lanes 1–3; cells treated with 10 μmoles/L, lanes 4–6; cells treated with 15 μmoles/L, lanes 7–9; cells treated with 20 μmoles/L, lanes 10–12.

The results in FIG. 7 show that NAD(P)H oxidase inhibition reduces DNA binding to the cyclic-AMP responsive element (CRE) but not to AP-1 or OCT-1. Throughout this application, various publication are referenced. The disclosures of these publications are hereby incorporated by reference into this application in order to more fully describe the states of the art to which this invention pertains.

Although the present invention has been described with reference to specific details of certain embodiments thereof, it is not intended that such details should be regarded as limitations upon the scope of the invention except as and to the extent that they are included in the accompanying claims.

What is claimed is:

1. A method for inhibiting NAD(P)H oxidase enzymes comprising treating a patient in need thereof with from 1 mg to 500 mg per day an amount of a dicoumarol effective to disrupt performance of the oxidase and production of its reactive oxygen species signaling products, wherein said treatment includes the treatment of ischemia-reperfusion injury syndromes such as myocardial infarction and stroke, lowering blood pressure, treatment of asthma and regulation of growth and proliferation of malignant melanoma cells.

2. The method for inhibiting NAD(P)H oxidase enzymes according to claim 1 wherein the amount of a dicoumarol is from 50 mg to 200 mg per day.

3. The method for inhibiting NAD(P)H oxidase enzymes according to claim 1 wherein dicoumarol is administered in an aerosol.

4. The method for inhibiting NAD(P)H oxidase enzymes according to claim 1 wherein dicoumarol is administered orally.

5. A method for inhibiting NAD(P)H oxidase enzymes comprising treating a patient in need thereof with an amount of dicoumarol effective to disrupt performance of the oxidase and production of its reactive oxygen species signaling products wherein said dicoumarol is administered in combination with vitamin K.

6. The method for inhibiting NAD(P)H oxidase enzymes according to claim 5 wherein the amount of a dicoumarol is from 1 mg to 500 mg per day.

7. The method for inhibiting NAD(P)H oxidase enzymes according to claim 5 wherein the amount of a dicoumarol is from 50 mg to 200 mg per day.

8. The method for inhibiting NAD(P)H oxidase enzymes according to claim 5 wherein dicoumarol is administered in an aerosol.

9. The method for inhibiting NAD(P)H oxidase enzymes according to claim 5 wherein dicoumarol is administered orally.

* * * * *

UNITED STATES PATENT AND TRADEMARK OFFICE
CERTIFICATE OF CORRECTION

PATENT NO. : 6,987,127 B2 Page 1 of 1
DATED : January 17, 2006
INVENTOR(S) : Kennedy It is certified that error appears in the above-identified patent and that said Letters Patent is hereby corrected as shown below:

Column 1,
Line 13, insert the following:
-- FEDERALLY SPONSORED RESEARCH OR DEVELOPMENT
This invention was made in part by U.S. government support under NIH Grants HL-40665, HL-61377, AR42426 and HL66767. --.

Signed and Sealed this

Twenty-third Day of May, 2006

JON W. DUDAS
*Director of the United States Patent and Trademark Office*